(12) United States Patent
Angibaud et al.

(10) Patent No.: US 11,950,820 B2
(45) Date of Patent: *Apr. 9, 2024

(54) MECHANICAL LIGAMENT BALANCING DEVICES

(71) Applicant: Exactech, Inc., Gainesville, FL (US)

(72) Inventors: Laurent Angibaud, Gainesville, FL (US); Michael Mauldin, Lake City, FL (US); Matt Rueff, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 206 days.

This patent is subject to a terminal disclaimer.

(21) Appl. No.: 17/700,304

(22) Filed: Mar. 21, 2022

(65) Prior Publication Data

US 2022/0202462 A1    Jun. 30, 2022

Related U.S. Application Data

(63) Continuation of application No. 17/349,370, filed on Jun. 16, 2021, now Pat. No. 11,278,338.
(60) Provisional application No. 63/039,729, filed on Jun. 16, 2020.

(51) Int. Cl.
*A61B 17/88* (2006.01)
*A61B 17/00* (2006.01)

(52) U.S. Cl.
CPC ...... *A61B 17/8869* (2013.01); *A61B 17/8858* (2013.01); *A61B 2017/00367* (2013.01)

(58) Field of Classification Search
CPC ............ A61B 17/8869; A61B 17/8858; A61B 17/025; A61B 2017/0268; A61B 2017/0275
See application file for complete search history.

(56) References Cited

U.S. PATENT DOCUMENTS

| | | | |
|---|---|---|---|
| 6,520,996 B1 | 2/2003 | Manasas et al. | |
| 6,610,092 B2 | 8/2003 | Ralph et al. | |
| 7,291,171 B2 | 11/2007 | Ferree | |
| 7,892,285 B2 * | 2/2011 | Viker | A61F 2/4611 623/17.13 |

(Continued)

OTHER PUBLICATIONS

International Search Report and Written Opinion from International Application No. PCT/US2021/037627 dated Sep. 24, 2021.

*Primary Examiner* — Tracy L Kamikawa
(74) *Attorney, Agent, or Firm* — GREENBERG TRAURIG, LLP

(57) ABSTRACT

A device including a first plate configured to interface with a first bone structure of a joint; a second plate configured to interface with a second bone structure of the joint opposite the first bone structure; and at least one mechanical actuation mechanism disposed between the first plate and the second plate and configured to apply a distraction force along an axis between the first plate and the second plate so as to urge the first plate and the second plate away from one another, wherein the device is configured so as to have a range of motion ranging from a minimum distance between the first plate and the second plate to a maximum distance between the first plate and the second plate, and wherein the mechanical actuation mechanism is configured such that the distraction force is substantially constant distraction force across the range of motion.

22 Claims, 21 Drawing Sheets

(56) References Cited

U.S. PATENT DOCUMENTS

| | | | |
|---|---|---|---|
| 8,313,529 B2* | 11/2012 | Lechmann | A61F 2/4425 623/17.16 |
| 9,216,097 B2* | 12/2015 | Hauri | A61B 17/025 |
| 9,615,935 B2 | 4/2017 | Patterson et al. | |
| 10,206,791 B2* | 2/2019 | D'Lima | A61F 2/4657 |
| 2005/0020941 A1 | 7/2005 | Tarabichi | |
| 2006/0149277 A1 | 7/2006 | Cinquin et al. | |
| 2006/0241569 A1 | 10/2006 | DiSilvestro | |
| 2009/0018544 A1 | 1/2009 | Heavener | |
| 2009/0222089 A1 | 9/2009 | Hauri et al. | |
| 2010/0249533 A1 | 9/2010 | Pierce et al. | |
| 2019/0008654 A1 | 1/2019 | Thommen et al. | |
| 2020/0155135 A1* | 5/2020 | Cole | A61B 17/8869 |

* cited by examiner

A. Above the threshold value:

B. Below the threshold value:

C. At the minimum height:

Impact of the load in the transversal plane:

| Sample | 9mm gap 1 | 9mm gap 2 | 9mm gap 3 | 12mm gap 1 | 12mm gap 2 | 12mm gap 3 | 15mm gap 1 | 15mm gap 2 | 15mm gap 3 |
|---|---|---|---|---|---|---|---|---|---|
| Ligament balancer 1 size 0 femur | 34.7 | 34.1 | 34.4 | 36.3 | 36.3 | 36.4 | 35.1 | 35.6 | 35.8 |
| Ligament balancer 1 size 3 femur | 34.0 | 33.8 | 34.2 | 37.8 | 37.6 | 38.2 | 34.1 | 34.4 | 35.2 |
| Ligament balancer 1 size 6 femur | 32.9 | 33.0 | 33.0 | 35.1 | 35.9 | 34.7 | 32.2 | 33.6 | 33.0 |
| Ligament balancer 2 size 0 femur | 34.3 | 34.0 | 34.2 | 37.8 | 37.0 | 38.2 | 33.7 | 33.8 | 34.0 |
| Ligament balancer 2 size 3 femur | 33.9 | 34.0 | 34.0 | 37.7 | 37.4 | 37.2 | 34.8 | 34.6 | 34.2 |
| Ligament balancer 2 size 6 femur | 33.1 | 33.2 | 33.1 | 36.3 | 36.6 | 36.4 | 32.6 | 33.0 | 33.8 |
| Ligament balancer 3 size 0 femur | 34.2 | 34.0 | 34.2 | 38.4 | 38.1 | 38.6 | 34.0 | 34.8 | 35.3 |
| Ligament balancer 3 size 3 femur | 33.8 | 34.0 | 34.0 | 37.9 | 36.6 | 36.5 | 34.5 | 34.7 | 34.5 |
| Ligament balancer 3 size 6 femur | 33.4 | 33.1 | 32.9 | 35.9 | 36.2 | 37.0 | 32.8 | 33.9 | 32.9 |
| Ligament balancer 4 size 0 femur | 33.2 | 33.4 | 33.5 | 36.4 | 36.1 | 36.9 | 33.8 | 34.5 | 34.1 |
| Ligament balancer 4 size 3 femur | 33.6 | 33.6 | 33.6 | 36.8 | 37.0 | 37.1 | 34.4 | 34.1 | 34.0 |
| Ligament balancer 4 size 6 femur | 32.7 | 32.6 | 32.1 | 35.6 | 35.7 | 35.8 | 32.3 | 33.0 | 33.0 |
| Ligament balancer 5 size 0 femur | 33.7 | 33.9 | 33.5 | 37.3 | 36.9 | 37.0 | 34.8 | 34.6 | 34.8 |
| Ligament balancer 5 size 3 femur | 33.2 | 33.2 | 33.2 | 36.7 | 36.9 | 36.7 | 34.7 | 33.9 | 33.8 |
| Ligament balancer 5 size 6 femur | 33.2 | 32.8 | 32.6 | 36.3 | 36.1 | 36.1 | 32.8 | 32.8 | 33.3 |
| Average of five ligament balancers (as measurements per gap size) | 33.5 | | | 36.8 | | | 34.0 | | |

Figure 19C

MECHANICAL LIGAMENT BALANCING DEVICES

CROSS-REFERENCE TO RELATED APPLICATION

This application is a continuation of U.S. patent application Ser. No. 17/349,370, filed Jun. 16, 2021 and entitled "MECHANICAL LIGAMENT BALANCING DEVICES", now U.S. Pat. No. 11,278,338, which is a Section 111(a) application relating to and claiming the benefit of commonly-owned, U.S. Provisional Patent Application No. 63/039,729, filed Jun. 16, 2020 and entitled "LIGAMENT BALANCING DEVICES.

FIELD OF THE INVENTION

The field of invention relates to orthopedic surgery. More particularly, the field of invention relates to balancing devices that are used by surgeons to characterize a ligament and capsular envelope around a joint during surgery and to apply a tension to the ligament and capsular envelope around a joint during the same surgery.

BACKGROUND OF THE INVENTION

Expandable ligament balancing devices are used to help the surgeon to assess the proper tension of the ligament envelope surrounding the joint at the time of the surgery. FIG. 1 shows a conventional ligament balancing device. These devices (e.g., devices disclosed by U.S. Pat. No. 10,154,836) include a proximal plate element 100, a distal plate element 200, and an expandable member 300 located between the proximal plate 100 and the distal plate 200. The expandable member 300 is controlled through an expansion mechanism using an electrical source, an electromechanical source, a mechanical source, a pneumatic source, a hydraulic source, or any combination of these sources.

Conventional ligament balancing devices have some limitations. A first limitation relates to the limited range of adjustment of the proximal plate 100 relative to the distal plate 200 in terms of height defined as the distance between the proximal plate 100 and the distal plate 200 (e.g., 8 to 14 mm), angular tilt defined as the sagittal and/or coronal orientation of the proximal plate 100 relative to the distal plate 200 (e.g., ±6°) and more importantly the interdependence between these two parameters. Based on the current architecture, the full range of angular tilt is only available when the height is above a threshold (e.g., at least between 10 and 12 mm), as shown in FIG. 2A. As the height is closer to its extreme minimum value, then the range of angular tilt is decreased. FIG. 2B shows a limited available range of angular tilt when the height of a conventional ligament balancing device on one side is below the threshold value. FIG. 2C shows the absence of available range of angular tilt when the height of a conventional ligament balancing device on one side is at its minimum (e.g., 8 mm). This limitation is particularly significant for bi-compartmental types of joints (e.g., during total knee arthroplasty), in which one compartment may be substantially tighter than the other compartment.

A second limitation relates to the impact of the loading condition between the considered joint and the mobile plate (i.e., the proximal plate 100 or the distal plate 200 depending on the indication) in the transversal plane on the height and angular tilt measurements. There are two individual sources of error regarding this limitation. The first source of error relates to the location of the load relative to the expandable member 300. With reference to FIG. 3, which shows a profile view of a conventional ligament balancing device, the location of the load application impacts the measured gaps and/or angular tilts. For example, when the application of the load is directly located "inside" the expandable transversal cross-section (Area A), then the impact is negligible. Area B: When the application of the load is located on the most posterior aspect or the most lateral aspect of the articular surface (Area B), then the impact may not be clinically relevant (e.g., ~0.5 mm). When the application of the load is located on the most anterior aspect of the articular surface (Area C), then the impact may be clinically relevant (e.g., more than 1 mm).

A third limitation relates to the source of error associated with the placement of the device in the frontal (e.g., coronal) plane as it would impact the distribution of the moment arms and therefore the balance. Similar to the discussion above, this is particularly significant for bi-compartmental joints.

A fourth limitation relates to the difficulty of maintaining a true force-controlled feedback loop of the expandable member. Therefore, depending on the height, the distraction force may fluctuate.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 12A-12F show a sixth exemplary ligament balancing device;

FIG. 19C shows a data table of test data.

SUMMARY OF THE DISCLOSURE

Figure 1:
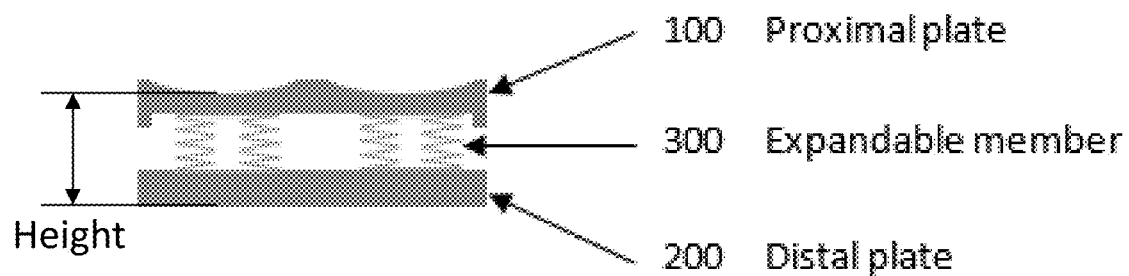
FIG. 1 shows a conventional ligament balancing device.
Figure 2A:
FIG. 2A shows the available range of tilt when the spacing (i.e., the height) of the ligament balancing device of FIG. 1 is above the threshold value.
Figure 2B:
FIG. 2B shows the available range of tilt when the spacing (i.e., the height) of the ligament balancing device of FIG. 1 is below the threshold value.
Figure 2C:
FIG. 2C shows the available range of tilt when the spacing (i.e., the height) of the ligament balancing device of FIG. 1 is at the high or low end of its spacing range.
Figure 3:
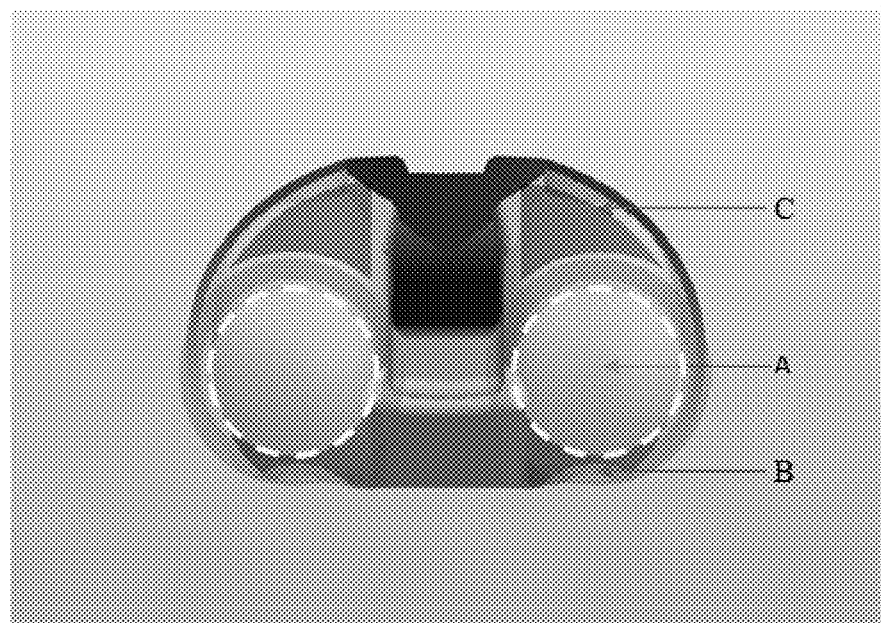
FIG. 3 shows an alternate view of the conventional ligament balancing device of FIG. 1.

In some embodiments, a device includes a first plate configured to interface with a first bone structure of a joint; a second plate configured to interface with a second bone structure of the joint opposite the first bone structure; and at least one mechanical actuation mechanism disposed between the first plate and the second plate and configured to apply a distraction force along an axis between the first plate and the second plate so as to urge the first plate and the second plate away from one another, wherein the device is configured so as to have a range of motion ranging from a minimum distance between the first plate and the second plate to a maximum distance between the first plate and the second plate, and wherein the mechanical actuation mechanism is configured such that the distraction force is substantially constant distraction force across the range of motion.

In some embodiments, the substantially constant distraction force is a distraction force that is within plus or minus fifteen percent of a nominal distraction force across the range of motion. In some embodiments, the substantially constant distraction force is a distraction force that is within plus or minus ten percent of a nominal distraction force across the range of motion.

In some embodiments, the at least one mechanical actuation mechanism includes: a first actuation sub-mechanism, and a second actuation sub-mechanism, wherein the first actuation sub-mechanism is configured to provide a first actuation sub-mechanism distraction force, and wherein the second actuation sub-mechanism is configured to provide a second actuation sub-mechanism distraction force that is antagonist to the first actuation sub-mechanism distraction force.

In some embodiments, the at least one mechanical actuation mechanism includes: at least one axial compression spring oriented along the axis, wherein an axial distraction force applied along the axis by the at least one axial compression spring increases as the first plate travels toward the second plate; and at least one diagonal compression spring oriented diagonally with respect to the axis, wherein an axial distraction force applied along the axis by the at least one diagonal compression spring decreases as the first plate travels toward the second plate, wherein the axial distraction force applied by the at least one axial compression spring and the axial distraction force applied by the at least one diagonal compression spring combine to produce the substantially constant distraction force. In some embodiments, the at least one diagonal compression spring is pivotably coupled to the first plate and to the second plate. In some embodiments, the device also includes a stability mechanism configured to maintain the first plate and the second plate substantially parallel with respect to one another. In some embodiments, the at least one axial compression spring is a peripheral spring positioned around the stability mechanism.

In some embodiments, the at least one mechanical actuation mechanism includes: an expandable member connecting the first plate to the second plate; and a spring positioned to apply a force to the expandable member so as to urge the first plate away from the second plate. In some embodiments, the force applied by the spring increases as the first plate approaches the second plate, the expandable member includes a pivot point, and the spring is configured such that a moment arm of the force applied to the spring about the pivot point decreases as the first plate approaches the second plate, whereby the spring applies the substantially constant distraction force. In some embodiments, the device also includes a second spring, wherein the device is configured such that the spring and the second spring are interchangeably positionable within the device, and wherein the further spring is configured to apply a further force that is different from the force applied by the spring, whereby the device applies a further substantially constant distraction force that is different from the substantially constant distraction force when the second spring is positioned within the device. In some embodiments, the device includes an adjustment mechanism that is adjustable by a user to pre-load the spring, whereby adjustment of the adjustment mechanism adjusts substantially constant distraction force. In some embodiments, the adjustment mechanism includes a set screw. In some embodiments, the spring is a leaf spring.

In some embodiments, the device is a monoblock device. In some embodiments, the device is a modular device configured for at least one of the first plate or the second plate to be removable from the at least one mechanical actuation mechanism.

In some embodiments, the device is configured to be used in a total knee arthroplasty, a unicompartmental knee arthroplasty, an anatomic total shoulder arthroplasty, a reverse total shoulder arthroplasty, or an ankle arthroplasty.

In some embodiments, the device also includes a second one of the first plate configured to interface with the first bone structure of the joint, and a second one of the mechanical actuation mechanism disposed between the second one of the first plate and the second plate and configured to apply a second distraction force along an axis between the second one of the first plate and the second plate so as to urge the second one of the first plate and the second plate away from one another, wherein the device is configured so as to have a range of motion ranging from a minimum distance between the second one of the first plate and the second plate to a maximum distance between the second one of the first plate and the second plate, and wherein the second one of the mechanical actuation mechanism is configured such that the second distraction force is substantially constant distraction force across the range of motion. In some embodiments, the second distraction force is different from the distraction force.

In some embodiments, the mechanical actuation mechanism is at least partially embedded within one of the first plate or the second plate.

In some embodiments, the device is sized to be positioned intra-articularly within the joint.

In some embodiments, the mechanical actuation mechanism is positioned within a perimeter of the first plate and within a perimeter of the second plate.

In some embodiments, a kit includes a first one of the device and a second one of the device. In some embodiments, the substantially constant distraction force of the first one of the device is greater than the substantially constant distraction force of the second one of the device. In some embodiments, the first one of the device and the second one of the device are configured to be joined to one another at the respective second plates thereof such that the distraction force of the first one of the device and the distraction force of the second one of the device are parallel to one another.

In some embodiments, a kit includes a plurality of first plates configured to interface with a first bone structure of a joint, wherein a first one of the plurality of first plates has a different sizes than a second one of the plurality of first plates; a plurality of plate assemblies, wherein each of the plurality of plate assemblies includes: a second plate configured to interface with a second bone structure of the joint opposite the first bone structure; at least one mechanical actuation mechanism fixed to the second plate and configured to be positioned between the second plate and a selected one of the plurality of first plates and configured to be coupled to the selected one of the first plates to form an assembled device, whereby the at least one mechanical actuation mechanism is configured to apply a distraction force along an axis between the selected one of the first plates and the second plate so as to urge the selected one of the first plates and the second plate away from one another, wherein the assembled device is configured so as to have a range of motion ranging from a minimum distance between the selected one of the first plates and the second plate to a maximum distance between the selected one of the first plates and the second plate, and wherein the at least one mechanical actuation mechanism is configured such that the distraction force is substantially constant distraction force across the range of motion.

In some embodiments, a method includes providing a device including a first plate configured to interface with a first bone structure of a joint; a second plate configured to interface with a second bone structure of the joint opposite the first bone structure; at least one mechanical actuation mechanism disposed between the first plate and the second plate and configured to apply a distraction force along an axis between the first plate and the second plate so as to urge the first plate and the second plate away from one another, wherein the device is configured so as to have a range of motion ranging from a minimum distance between the first plate and the second plate to a maximum distance between the first plate and the second plate, and wherein the mechanical actuation mechanism is configured such that the distraction force is substantially constant distraction force across the range of motion; performing a cut to a bone of a joint of a patient so as to produce a cut surface of the bone; positioning the device within the joint of the patient such that the second plate abuts the cut surface; and characterizing laxity of ligaments of the joint of the patient while the device is positioned within the joint.

DETAILED DESCRIPTION OF THE DRAWINGS

The exemplary embodiments relate to ligament balancing devices that address the shortcomings described above. In some embodiments described herein, exemplary ligament balancing devices will be described with reference to the total knee joint. In such devices, a first plate (e.g., a proximal plate) is configured to contact the distal aspect of a patient's femur (e.g., the patient's native femur), a trial femoral component, or a femoral component depending on the stage of the surgery (e.g., whether performed prior to or subsequent to femoral cuts); and a second plate (e.g., a distal plate is configured to contact a proximal end of the patient's tibia (e.g., a cut surface of a proximal end of the tibia). However, it will be apparent to those of skill in the art that the broader principles of this disclosure would apply to any joint. For example, it will be apparent to those of skill in the art that the exemplary embodiments can be divided into two at the level of the sagittal plane of symmetry and each side specific sub-component can be used for partial knee joint or total knee joint where the cruciate ligaments are maintained in place. Similarly, it will be apparent to those of skill in the art that exemplary ligament balancing devices may be adapted for use in other joints, such as a shoulder joint (in which case a first plate may be a medial plate and a second plate may be a lateral plate or vice versa), an ankle joint, a hip joint, an elbow joint, etc. The exemplary embodiments described herein use the term "plate" to refer to various elements that are adapted to act as points of contact between the exemplary ligament balancing devices described herein and the bony surfaces of a joint. It will be apparent to those of skill in the art that the specific shapes of plates described herein are only exemplary and that other differently shaped contact elements are possible without departing from the broader concepts disclosed herein. For example, a plate need not include a contiguous and/or uninterrupted contact surface, and may include one or more holes or other interruptions therein.

Figure 4:
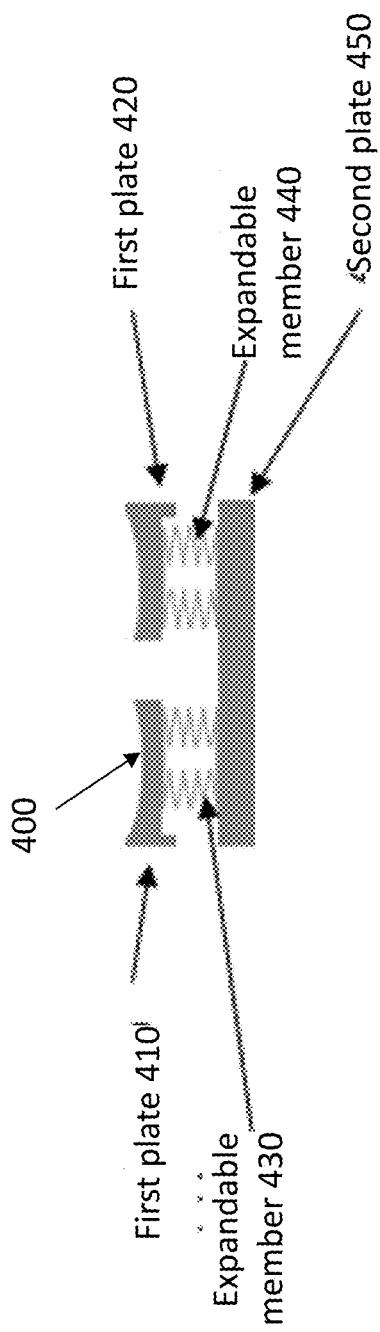
FIG. 4 shows a first exemplary ligament balancing device.
Figure 5:
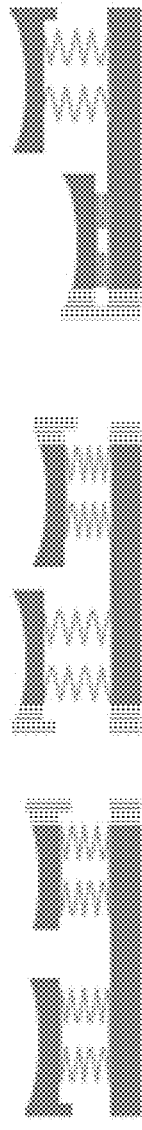
FIG. 5 shows various types of motion of the exemplary ligament balancing device of FIG. 4.

FIG. 4 shows a first exemplary ligament balancing device 400. In some embodiments, an exemplary ligament balancing device includes two separate first plates 410 and 420, wherein the first one of the first plate 410 is intended to engage with the first condyle of the femur and the second one of the first plate 420 is intended to engage with the second condyle of the femur. In some embodiments, a first expandable member 430 is located between the first one of the first plate 410 and a second plate 450 and a second expandable member 440 is located between the second one of the first plate 420 and the distal plate 450. The first expandable member 430 and the second expandable member 440 can be controlled by the same expansion mechanism or separate expansion mechanisms. In such embodiments, the range of angular tilt is not linked to (and therefore not limited by) the value of the height. For example, as shown in FIG. 5, if the first one of the first plate 410 is in a fully collapsed position with respect to the second plate 450, then the second one of the first plate 420 can still independently self-adjust through its entire range of height depending on the ligament laxity.

Figure 6:
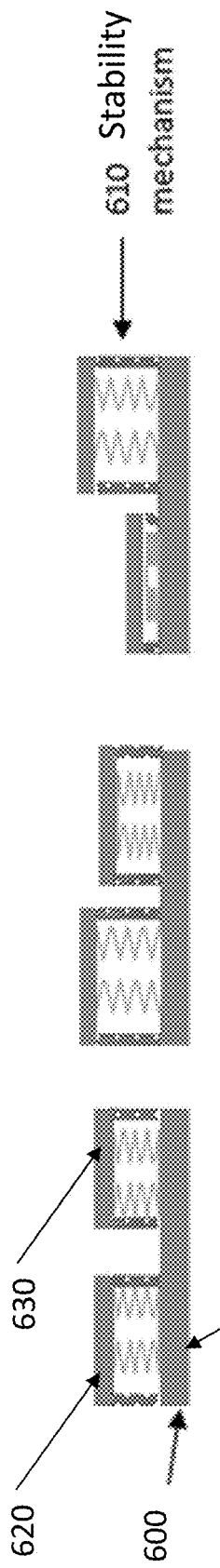
FIG. 6 shows a second exemplary ligament balancing device.

FIG. 6 shows a second exemplary ligament balancing device 600. The second embodiment includes a stability mechanism 610 (e.g., hinged lever arms, telescopic posts) to constrain the degree of freedom of the first one of the first plate 620 and the second one of the first plate 630 relative to the second plate 640. In some embodiments, the only degree of freedom of the first plates 620, 630 relative to the distal plate 640 relates to the translation along an axis substantially perpendicular to the contact surface of the second plate 640, which should equal to the proximal-distal axis in absence of posterior tibial slope and *varus*/valgus of the proximal tibial cut. In some embodiments, the contact surfaces of the first plates 620, 630 are substantially flat (e.g., as shown in FIG. 6); whereas in other embodiments, the contact surfaces of the first plates 620, 630 are essentially convex or concave, which, in the case of a device 600 adapted for use in total knee arthroplasty, would mimic the anatomy of the proximal end of a native tibia.

As a result of the exemplary embodiments, such as the embodiments described above with reference to the FIG. 6 (i.e., having the features of (1) limiting the degree of freedom of the first plates 620, 630 relative to the second plate 640 to a translation along a single axis substantially perpendicular to the contact surface of the second plate 640 and (2) having the contact surfaces of the first plates 620, 630 to be substantially flat or essentially convex or essentially concave) four benefits can be achieved. First, in some embodiments, the ligament balancing device 600 allows the measure of the true joint gap through the entire range of motion to be defined as the distance between the most distal point of each condyle to the simulated proximal tibial cut, which is not achievable with conventional ligament balancing devices as the angular tilt of the proximal plate would not allow such measurement. Second, in some embodiments, due to the added mechanical constraint offered by the stability mechanism 610, the exemplary ligament balancing device 600 has increased stability (e.g., rigidity) properties, thereby eliminating (or at least attenuating) the effect of the loading condition on the measured gaps and eliminating (or at least attenuating) the effect of the medial and lateral contact points on the measured gaps. Third, in some embodiments, the stability mechanism 610 can be used to create a physical stop to limit the range of translation of the first plates 620, 630 relative to the second plate 640. Fourth, in some embodiments, by selecting the shape of the contact surfaces of the first plates 620, 630 (e.g., essentially concave on the medial side and substantially flat on the lateral side), the surgeon can perform the acquisition of the true joint gap through the entire range of motion according a femoro-tibial constraint intended to simulate the final implant geometry. The advantages of the device 600 are described above with specific reference to the device 600 as adapted for use in total knee arthroplasty, but it will be apparent to those of skill in the art that similar advantages may be achieved through use of the device 600 as adapted for use in other types of joint surgeries.

Figure 7:
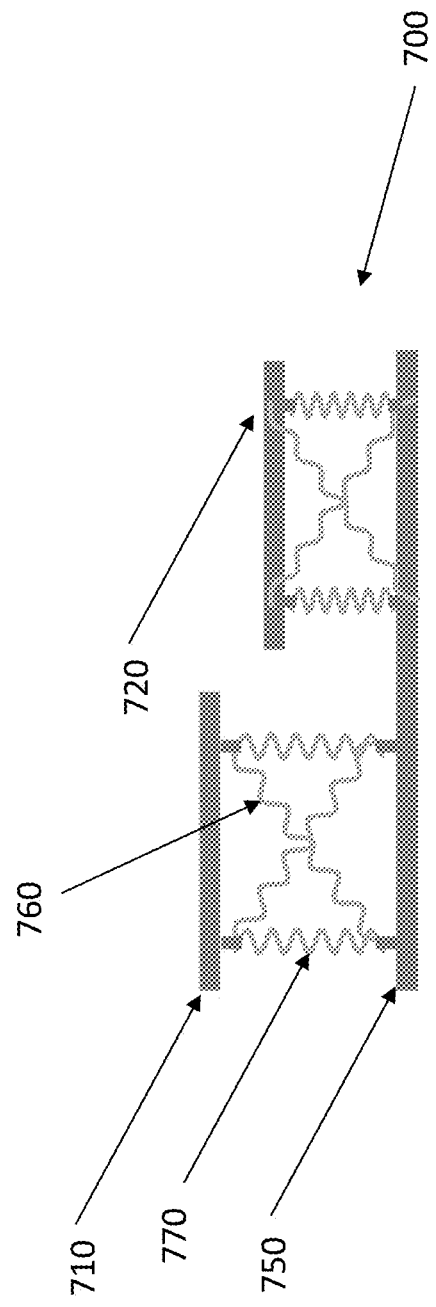
FIG. 7 shows a third exemplary ligament balancing device.

FIG. 7 shows a third exemplary ligament balancing device 700. In some embodiments, each expandable member or aspects of the expandable member can act by itself act as the stability mechanism. With reference to the embodiment of FIG. 7, the expandable member features flexures that generate substantially constant distraction force between the first plate and the second plate across the range of motion of the first plate relative to the second plate while acting as the stability mechanism. For example, the embodiment can feature a first set of springs 760 that compress in an axial direction (e.g., along an axis that is perpendicular to the bone contacting surface of the second plate 750) and a second set of springs 770 that are defeated in compression, where the first set of springs is not linearly aligned with the second set of springs. In some embodiments, the first set of springs 760 and the second set of springs 770 can be referred to collectively as an actuation mechanism, e.g., a mechanical actuation mechanism. In some embodiments, such an orientation results in generating a roughly constant force (e.g., within ±5% of a nominal force, or within ±10% of a nominal force, or within ±15% of a nominal force) between the first plate 710 or 720 and the second plate 750 regardless of the distance/height between the first plate 710 or 720 and the second plate 750. As a result, the combination of the at least two sets of springs acts as a force stabilizing mechanism. Two such constant force embodiments featuring the first plates 710, 720 and the second plate 750 could be joined at the level of the second plate 750 to allow concomitant constant force application to two sides of a bicondylar joint independently. For example, in an embodiment of the device 700 that is adapted for use in a knee joint, the device may include a single second plate 750, which is adapted to interface with a patient's tibia, and two first plates 710 and 720, one of which is adapted to interface with a medial condyle of the patient's femur and one of which is adapted to interface with a lateral condyle of the patient's femur, and both of which are coupled to the same second plate 750.

As used herein, the terms "substantially constant distraction force" and "quasi-constant force," as used to describe the distraction force applied by an exemplary ligament balancing device across an available range of motion of such a ligament balancing device (e.g., from a most compressed position to a most expanded position), refers to a force that varies by no more than a certain variance percentage as compared to a nominal distraction force (i.e., is no more than the certain percentage greater than or less than the nominal distraction force). For example, if the nominal distraction force of an exemplary ligament balancing device is ten (10) pounds and the certain percentage is 10%, then a "substantially constant distraction force" is a force that is within plus or minus 10% of the nominal value of ten (10) pounds, i.e., is between nine (9) and eleven (11) pounds. In some embodiments, the variance percentage is 5%. In some embodiments, the variance percentage is less than or equal to 5%. In some embodiments, the variance percentage is 10%. In some embodiments, the variance percentage is less than or equal to 10%. In some embodiments, the variance percentage is 11%. In some embodiments, the variance percentage is less than or equal to 11%. In some embodiments, the variance percentage is 12%. In some embodiments, the variance percentage is less than or equal to 12%. In some embodiments, the variance percentage is 13%. In some embodiments, the variance percentage is less than or equal to 13%. In some embodiments, the variance percentage is 14%. In some embodiments, the variance percentage is less than or equal to 14%. In some embodiments, the variance percentage is 15%. In some embodiments, the variance percentage is less than or equal to 15%. In some embodiments, the variance percentage is 16%. In some embodiments, the variance percentage is less than or equal to 16%. In some embodiments, the variance percentage is 17%. In some embodiments, the variance percentage is less than or equal to 17%. In some embodiments, the variance percentage is 18%. In some embodiments, the variance percentage is less than or equal to 18%. In some embodiments, the variance percentage is 19%. In some embodiments, the variance percentage is less than or equal to 19%. In some embodiments, the variance percentage is 20%. In some embodiments, the variance percentage is less than or equal to 20%.

Figure 8:
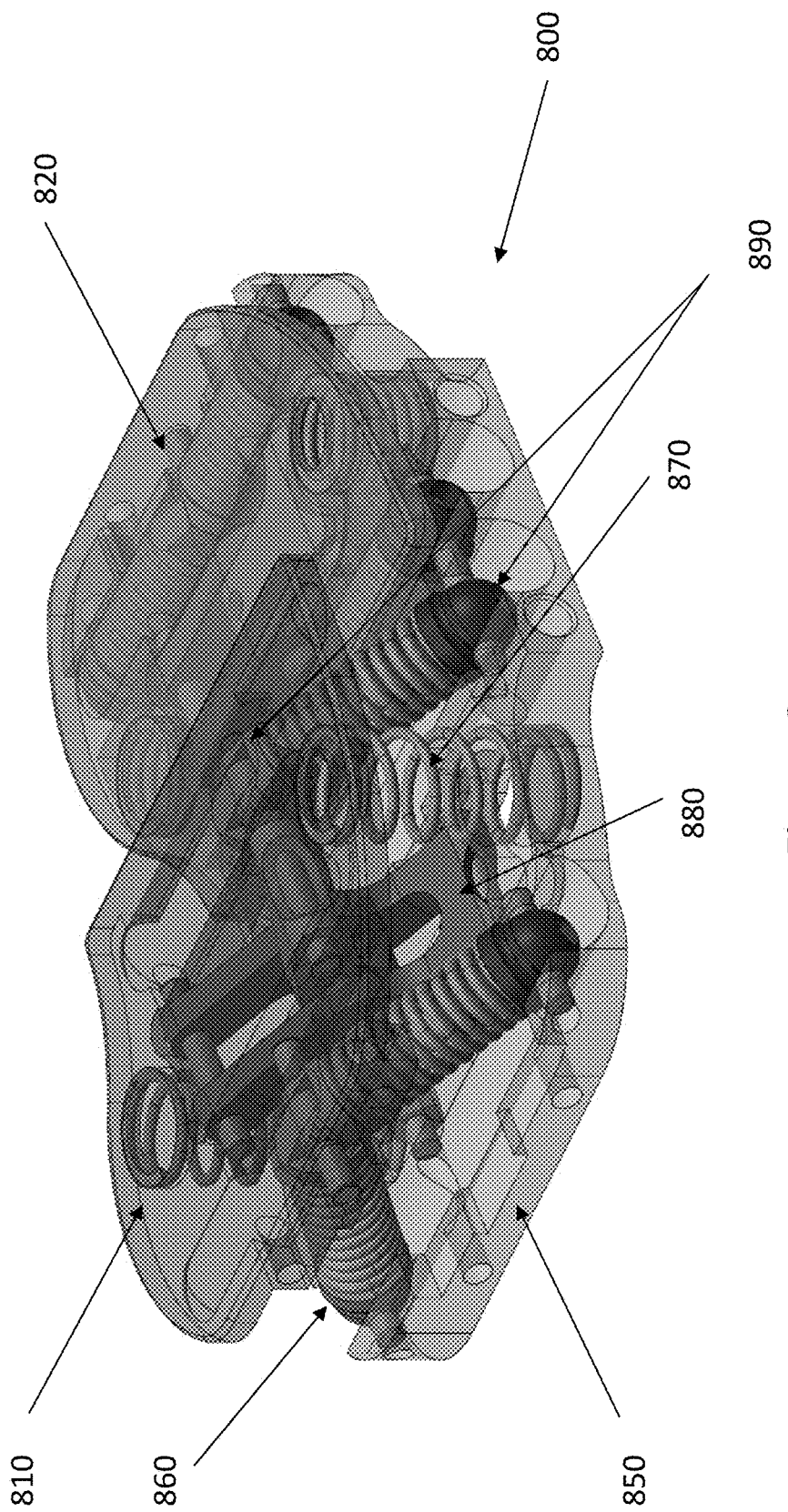
FIG. 8 shows a fourth exemplary ligament balancing device.

FIG. 8 illustrates a rendering of a fourth exemplary ligament balancing device 800 derived from the third exemplary ligament balancing device 700. In the exemplary device 800, the expandable member comprises two families of springs 860, 870. In some embodiments, the spring families 860, 870 can be referred to collectively as an actuation mechanism, e.g., a mechanical actuation mechanism. In some embodiments, the spring families 860, 870 are stabilized and the force is applied to the tibial and femoral members through interior pistons 890 that prevent buckling in the case of compression springs. In some embodiments, the pistons 890 are pivotably coupled to the tibial and femoral members (e.g., with lubricious dowels) to reduce friction within this embodiment. In some embodiments, in addition to the stability generated by the disposition of the two families of springs 860, 870, a side stability mechanism 880 is provided to enhance the stability of the first plate 810 and/or 820 relative to the second plate 850. In some embodiments, the spring families 860 and 870 are positioned and aligned in such a way that the applied force minimizes the engagement of the side stability mechanism and intrinsically reduces any frictional forces within the manifestation.

Figure 9A:
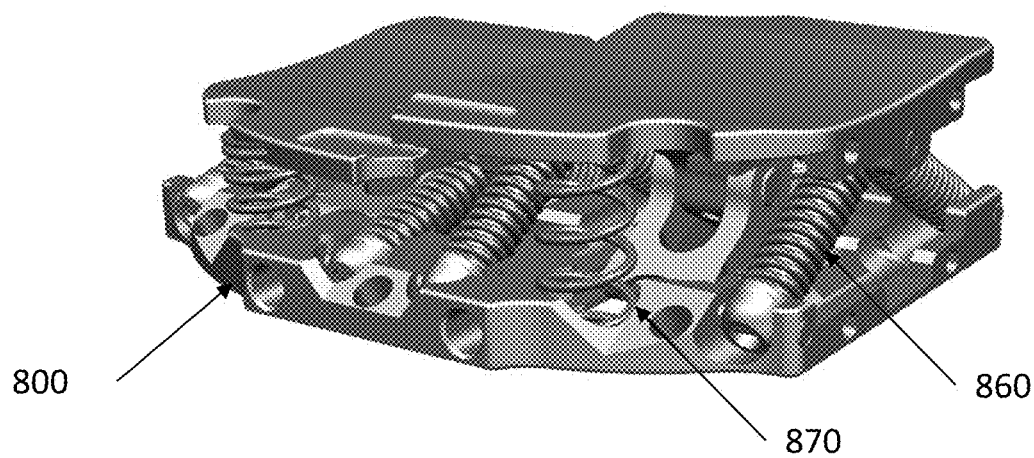
FIG. 9A shows a product representation of the fourth exemplary ligament balancing device.
Figure 9B:
FIG. 9B shows a graph of force applied by an axial spring of the product shown in FIG. 9A.
Figure 9C:
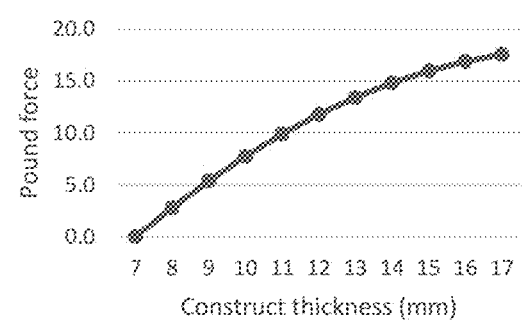
FIG. 9C shows a graph of force applied by a diagonal spring of the product shown in FIG. 9A.
Figure 9D:
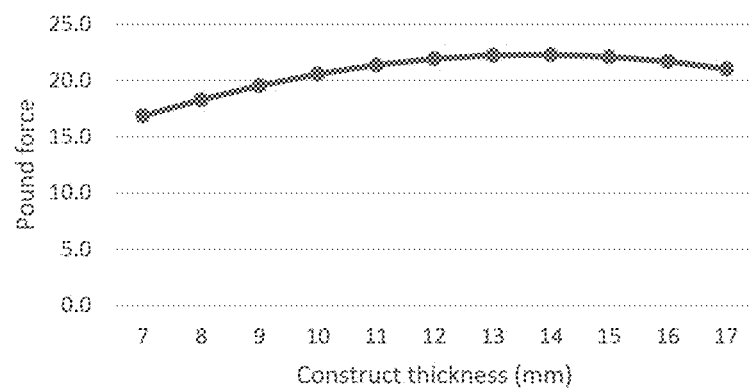
FIG. 9D shows a graph of the sum of forces applied by the axial spring and the diagonal spring of the product shown in FIG. 9A.

FIGS. 9A-9D illustrate manner in which the spring families 860, 870 cooperate to maintain a substantially constant axial distraction force between the first plate 810 or 820 and the second plate 850 regardless of the distance/height between the first plate 810 or 820 and the second plate 850. FIG. 9A shows locations of the spring families 860, 870 within the device 800. In some embodiments, the spring families 860, 870 can be referred to collectively as an actuation mechanism, e.g., a mechanical actuation mechanism. As shown in FIG. 9A, spring families 860 can also be referred to as diagonal springs, and spring families 870 can also be referred to as axial springs. FIG. 9B shows the distraction force applied by the axial springs 870 along the range of motion of the first plate 810 or 820. In some embodiments, the distraction force applied by the axial springs 870, as measured along the axial axis of the device 800, correlates directly with Hooke's Law, as a result of which the distraction force applied by the axial springs 870 is directly (e.g., linearly) proportional to displacement of the first plate 810 or 820 towards the second plate 850. FIG. 9C shows the distraction force applied by the diagonal springs 860 in the axial direction along the range of motion of the first plate 810 or 820. In some embodiments, due to the orientation of the diagonal springs 860, the distraction force applied by the diagonal springs 860 in the axial direction decreases as the first plate 810 or 820 approaches the second plate 850. This is the case because while the length of the diagonal springs 860 decreases, causing the overall force applied thereby to increase, the change in orientation of the diagonal springs 860 as the first plate 810 or 820 approaches the second plate 850 causes a greater proportion of the overall force applied by the diagonal springs 860 to be applied in a transverse direction rather than in an axial direction. The combination of the axial force applied by the axial springs 870 and the axial force applied by the diagonal springs 860 produces a total axial distraction force applied between the first plate 810 or 820 and the second plate 850. FIG. 9D shows the total distraction force, which is the sum of the forces shown in FIGS. 9B and 9C. In some embodiments, the characteristics of each individual spring forming of the spring families 860, 860, as well as their number and orientation, are engineered such that (1) the total axial distraction force is compatible with the desired use of the device 800 (e.g., to provide an axial distraction force of 20 pounds per compartment for a knee application or 40 pounds for a shoulder application), and (2) the axial force applied by the axial springs 870 across the range of expansion is substantially antagonist with the axial force applied by the diagonal springs 860 across the range of expansion, thereby to provide a substantially constant distraction force across the range of expansion.

Figure 9E:
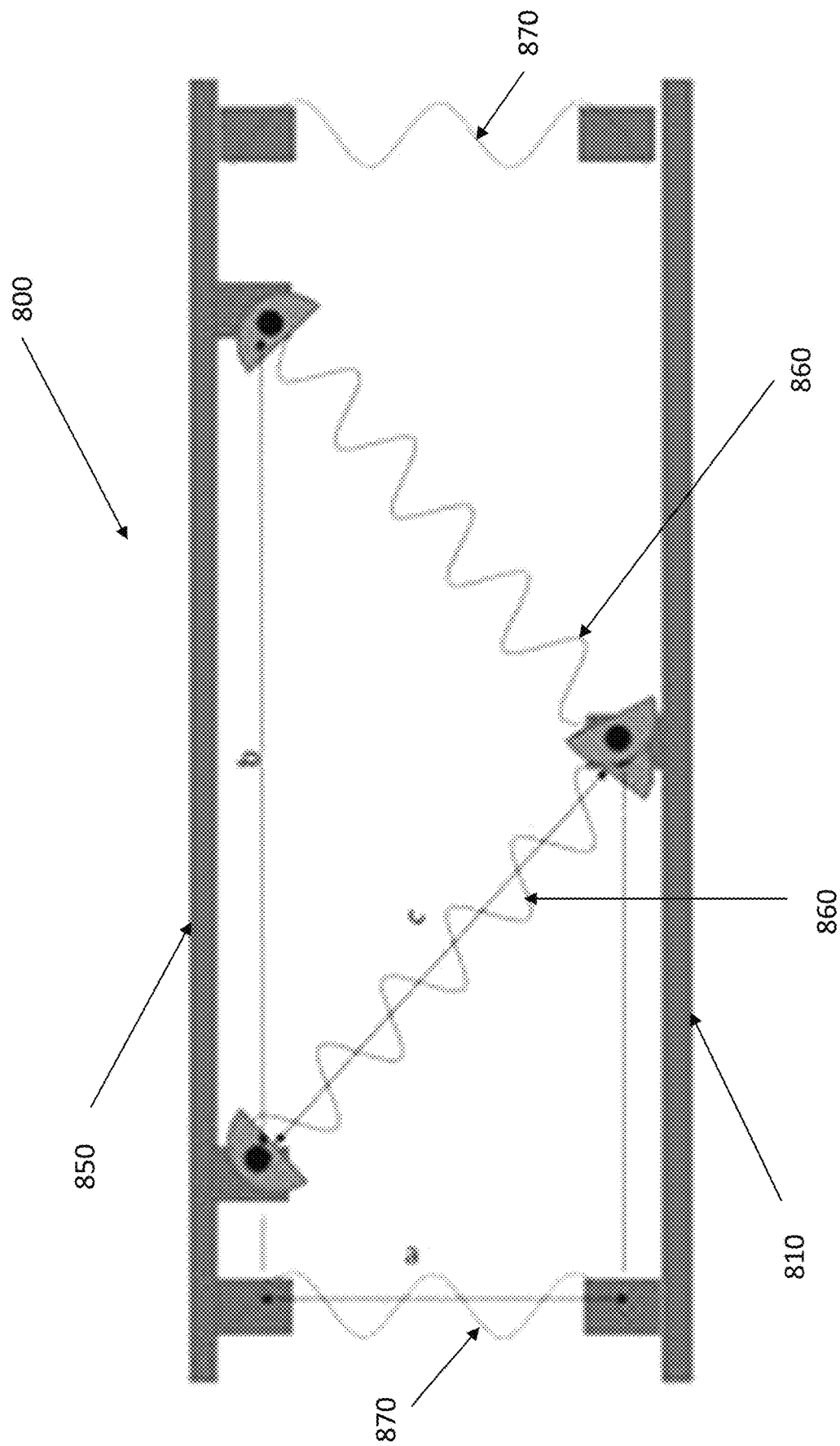
FIG. 9E shows a side schematic view of springs of the product shown in FIG. 9A.

For illustration of the manner in which the diagonal springs 860 and the axial springs 870 cooperate to provide a substantially constant distraction force, FIG. 9E shows a side view of the exemplary device 800 including the diagonal springs 860 and the axial springs 870. In FIG. 9E, dimension a refers to the current vertical length of the diagonal springs 860, dimension b refers to the transverse distance between the pivot points of two cooperating diagonal springs 860, and dimension c refers to the current length of the diagonal springs 860. The total force F applied by the combination of the diagonal springs 860 and the axial springs 870 can be expressed as F=V+D, where V is the force provided by the axial springs 870 and D is the force provided in the axial direction by the diagonal springs 860. The force V can be calculated as $V=k_v*x*n_v$, where $k_v$ is the spring constant of the axial springs 870, x is the displacement of the axial springs 870 from their uncompressed state, and $n_v$, is the quantity of the axial springs 870. In the embodiment shown in FIGS. 8 and 9A, two of the axial springs 870 are present for each of the first plates 810, 820, though this quantity may differ in other embodiments.

Continuing to refer to FIG. 9E, the force D can be calculated using the expression $$D = (L_d - (c_0 - c_x)) * k_d * \sin\left(\tan^{-1}\left(\frac{ax}{\frac{b}{2}}\right)\right) * 2 * n_d,$$

in which $L_d$ is the free length of one of the diagonal springs 860; $c_0$ is the length of one of the diagonal springs 860 when the device 800 in the uncompressed state (e.g., is fully expanded); $c_x$ is the length of the spring in the state at a point of interest (e.g., $c_1$ refers to the length of one of the diagonal springs 860 when the device 800 was compressed by 1 millimeter and $c_{10}$ refers to the length of one of the diagonal springs 860 when the device 800 was compressed by 10 millimeters); $k_d$ is the spring constant of the diagonal springs 860; ax is the vertical component of the diagonal springs 860 at the point of interest (e.g., $a_0$ refers to the length of the vertical component of one of the diagonal springs 860 in an uncompressed device 800 and $a_{10}$ refers to the length of the vertical component of one of the diagonal springs 860 when the device is compressed by 10 millimeters); b is the transverse distance between the pivot points of two cooperating diagonal springs 860; and nd is the number of diagonal spring pair mechanisms. In the embodiment shown in FIGS. 8 and 9A, two pairs of the diagonal springs 860 are present for each of the first plates 810, 820, though this quantity may differ in other embodiments.

Figure 10A:
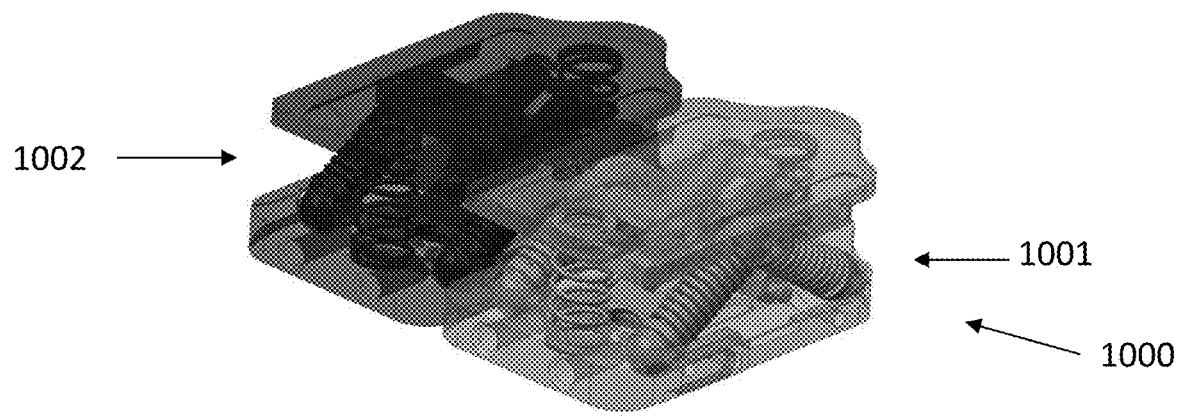
FIGS. 10A-10C show another product representation from any of the exemplary ligament balancing devices.
Figure 10B:
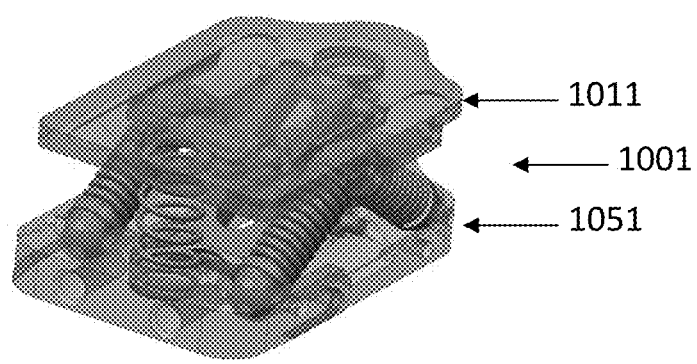
Figure 10C:
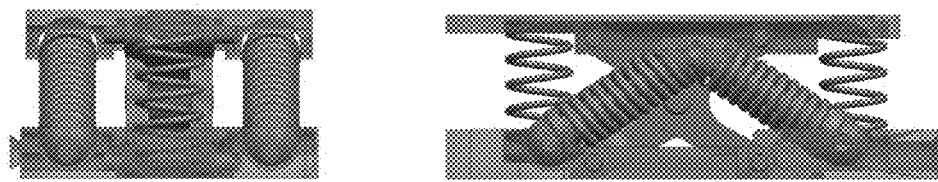

FIGS. 10A-10C illustrate renderings of a ligament balancing device 1000 including side specific modules 1001, 1002. In some embodiments, the ligament balancing device 1000 is similar to one of the ligament balancing devices 400, or 500, or 600, or 700, or 800, and is divided at the level of the sagittal plane of symmetry. In some embodiments, each side specific module 1001, 1002 includes a first plate (e.g., a proximal femoral plate) 1011, 1012, respectively, and a second plate (e.g., a distal tibial plate) 1051, 1052, respectively. In some embodiments, the modules 1001, 1002 are linked together using a mechanical connection (e.g., a dovetail mechanism, a separate clip, etc.). In some embodiments, each of the modules 1001, 1002 can be used individually (e.g., in the case of a partial knee joint), together with one another but not directly linked (e.g., in the case of bi-partial knee joint or total knee joint with conservation of the cruciate ligaments), or together and linked (e.g., in the case of total knee joint). In some embodiments, the modules 1001, 1002 are available under different configurations. In some embodiments, the ligament balancing device 1000 is provided as a kit (e.g., including the modules 1001 and 1002) and the surgeon assembles the desired combination at the time of surgery. In some embodiments, the surgeon selects and obtains (e.g., orders) the proper element(s) of the ligament balancing device 1000 (e.g., selects either the module 1001, the module 1002, or both) before surgery. In some embodiments, selection of the proper element(s) of the ligament balancing device 1000 is made based at least in part on a pre-operative imaging modality. In some embodiments, selection of the proper element(s) of the ligament balancing device 1000 is linked with pre-operative templating that predefines both the proper element(s) of the ligament balancing device and the size of the implant(s) to be used.

In some embodiments, the modules 1001, 1002 are available under different stiffness levels (e.g., low, medium, or high distraction force) of the expandable member. In such embodiments, the surgeon is able to select the proper stiffness level depending on the patient (e.g., high stiffness for high BMI patient or patient requiring more stability, low stiffness for low BMI patient). In addition, in such embodiments, the surgeon can leverage this option to tailor the stiffness depending on the considered compartment, as it has been established that the medial collateral envelope is stiffer than the lateral collateral ligament structure. Therefore, in such embodiments, surgeon can use a stiffer module for the medial compartment than the lateral compartment.

In some embodiments, the modules 1001, 1002 are available under different sizes in the transversal plane (e.g., small, large, etc). In such embodiments, this option can advantageously be leveraged to better fit the size of the knee joint, including in cases there is a substantial difference of size between the medial compartment and the lateral compartment. For example, such embodiments may provide the option for the surgeon to use a smaller size (along the anterior-posterior axis) on the lateral compartment than the medial compartment.

In some embodiments, the proximal aspects of the first plates of the modules 1001, 1002 are available under different geometries (e.g., flat, concave, or convex). In some such embodiments, because the proximal aspect of the native tibia is concave on the medial compartment and convex on the lateral compartment, the surgeon can select a proper combination to reproduce this native characteristic.

Figure 11:
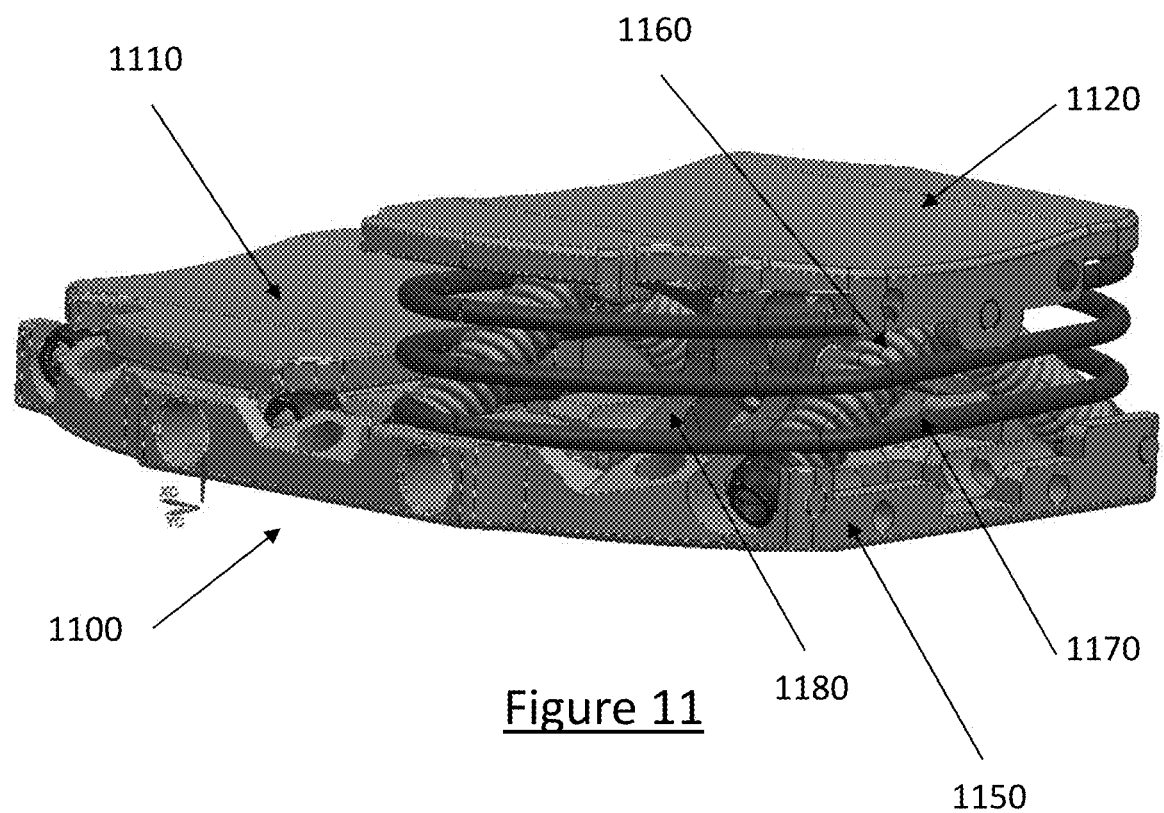
FIG. 11 shows a fifth exemplary ligament balancing device.

FIG. 11 shows a fourth exemplary ligament balancing device 1100 that is a variant of the fourth exemplary ligament balancing device 800. In the embodiment shown in FIG. 11, the device 1100 includes a peripheral spring 1170 rather than the axial springs 870 shown in FIG. 8. In some embodiments, the peripheral spring 1170 is substantially included within the perimeter of the first plate 1110 or 1120. For example, in some embodiments, the peripheral spring 1170 is positioned entirely within the perimeter of the first plate 1110 or 1120; on some embodiments, the peripheral spring 1170 mimics (e.g., is coextensive with) the perimeter of the first plate 1110 or 1120. In some embodiments, the device 1100 includes diagonal springs 1160 that are substantially similar to the diagonal springs 860 shown in FIG. 8. In some embodiments, diagonal springs 1160 and the peripheral spring 1170 can be referred to collectively as an actuation mechanism, e.g., a mechanical actuation mechanism. In some embodiments, the device 1100 includes a stability mechanism 1180 that is substantially similar to the stability mechanism 880 shown in FIG. 8. In some embodiments, by using a peripheral spring 1170, the stability mechanism 1180 configure to maintain the first plate 1110 or 1120 substantially parallel to the second plate 1150 can be of an extended length, thereby increasing the possible range of expansion of the first plate 1110, 1120 relative to the second plate 1150.

Figure 12A:
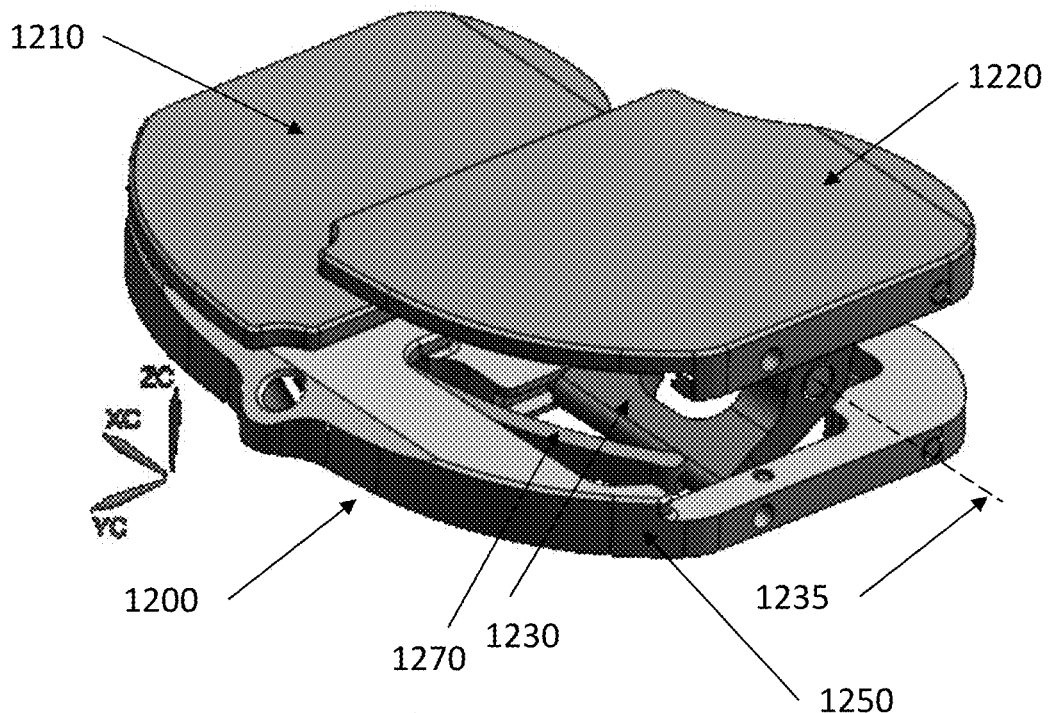
Figure 12B:
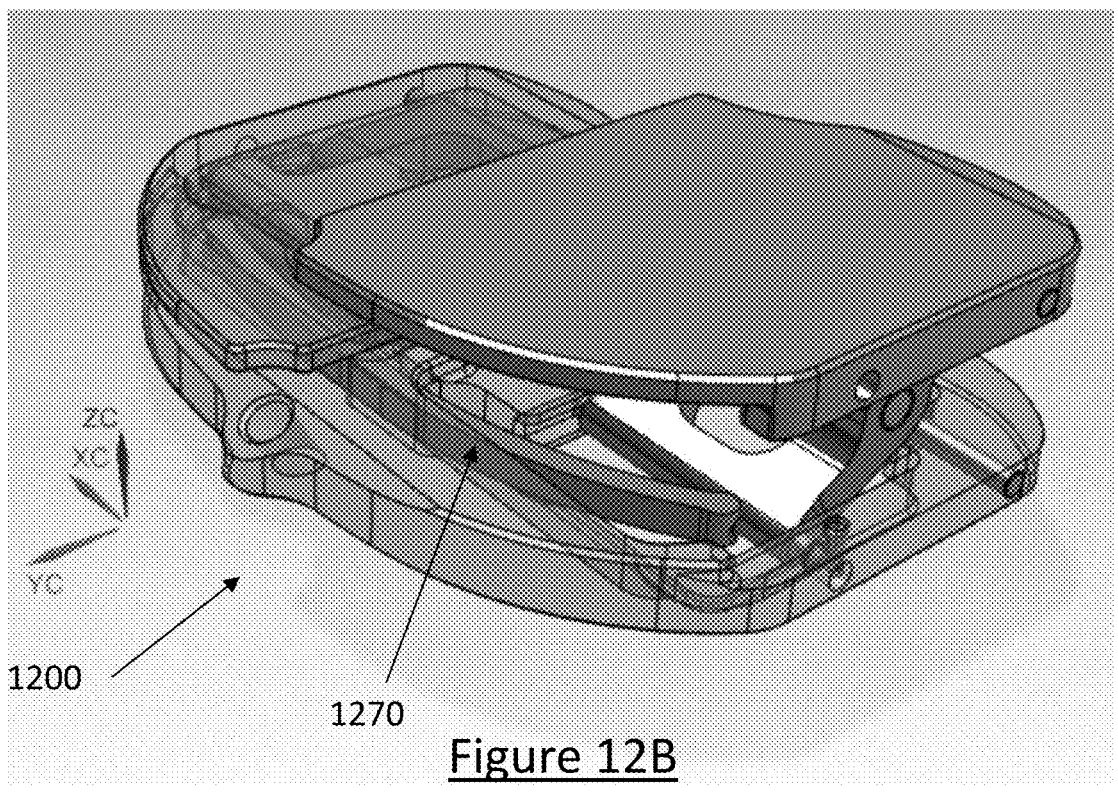

FIGS. 12A-12E shows a fifth exemplary ligament balancing device 1200. FIG. 12A shows a rendering of the device 1200 and FIG. 12B shows an alternate rendering of the device 1200 in which certain elements of the device 1200 are rendered in a partially transparent manner so as to facilitate visibility of other elements of the device 1200. In some embodiments, the device 1200 includes two first plates 1210, 1220 and a second plate 1250. In some embodiments, the sixth exemplary ligament balancing device 1200 is similar to the fourth exemplary ligament balancing device 800 in that it maintains substantially constant axial distraction force between the first plate 1210 or 1220 and the second plate 1250 regardless of the distance between the particular first plate 1210 or 1220 and the second plate 1250. In some embodiments, the device 1200 uses a different exemplary mechanically actuated intraarticular mechanism from those described above. In some embodiments, the device 1200 includes an expandable member 1230 that also acts as a stability mechanism 1260. In some embodiments, the device 1200 includes a leaf spring 1270. In other embodiments, the device 1200 may include a different type of spring. In some embodiments, the stability mechanism 1260 and the leaf spring 1270 can be referred to collectively as an actuation mechanism, e.g., a mechanical actuation mechanism. In some embodiments, the expandable member 1230 includes a pivot axis 1235, resulting into first moment arm between the pivot axis 1235 and the first plate 1210 or 1220, and a second moment arm between the pivot axis 1235 and the second plate 1250. In some embodiments, the expandable member 1230 and the leaf spring 1270 are designed such that a change in compression of the leaf spring 1270 due to the translation of the first plate 1210, 1220 relative to the second plate 1250 is substantially compensated for by the variation of the ratio between the first and second moment arms, so that the distraction force applied to the joint though the first plate 1210 or 1220 and the second plate 1250 is maintained substantially constant regardless of the distance between the first plate 1210 or 1220 and the second plate 1250.

Figure 12C:
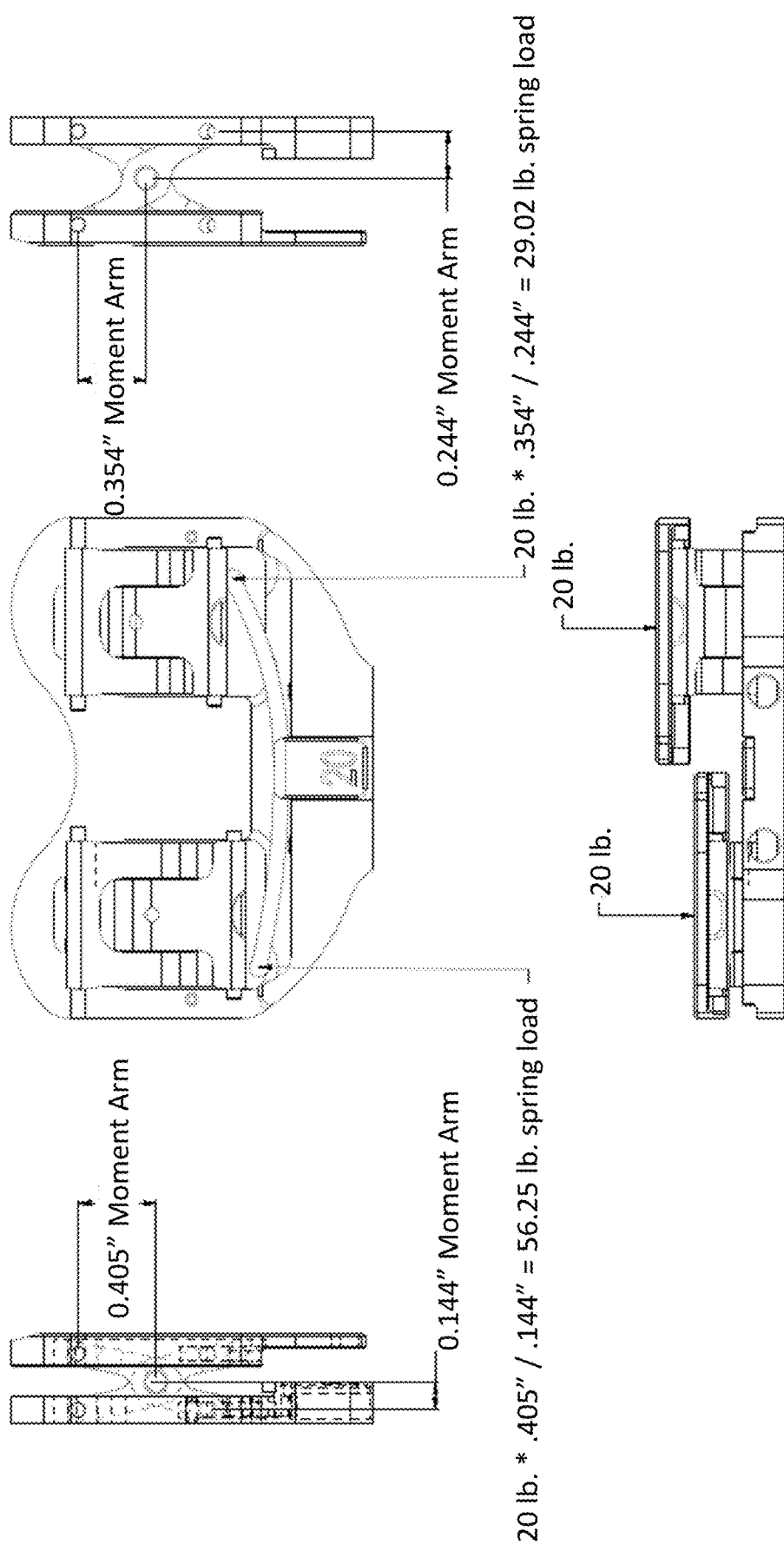

FIG. 12C shows a more detailed illustration of the different moment arms present within the device 1200 that result in the application of a substantially constant axial distraction force as described above. As shown in FIG. 12C, the force applied to the first plate 1210 or 1220 as a result of the action of the leaf spring 1270 is controlled by the moment arm of the force applied by the leaf spring 1270 about the pivot point of the expandable member 1230, as well as the moment arm of the output force applied to the first plate 1210 or 1220 about the pivot point of the expandable member 1230.

In the position of the device 1200 shown in FIG. 12C, the first plate 1210 is positioned in a compressed position with respect to the second plate 1250, as a result of which the leaf spring 1270 applies a force of 56.25 pounds to the expandable member 1230 coupled to the first one of the first plate 1210. In this position, the moment arm for the leaf spring 1270 is 0.144 inches, causing a moment of 56.25 pounds*0.144 inches=8.1 pound-inches about the pivot point of the expandable member 1230. In this same position, the moment arm of the force applied to the first one of the first plate 1210 is 0.405 inches. In this position, the force applied at the first one of the first plate 1210 as a result of the moment calculated above is 8.1 pound-inches/0.405 inches=20 pounds.

In the same position of the device 1200 shown in FIG. 12C, the second one of the first plate 1220 is positioned in an expanded position with respect to the second plate 1250, as a result of which the leaf spring 1270 applies a force of 29.02 pounds to the expandable member 1230 coupled to the second one of the first plate 1220. In this position, the moment arm for the leaf spring 1270 is 0.244 inches, causing a moment of 29.02 pounds*0.244 inches=7.08 pound-inches about the pivot point of the expandable member 1230. In this same position, the moment arm of the force applied to the second one of the first plate 1220 is 0.354 inches. In this position, the force applied at the second one of the first plate 1220 as a result of the moment calculated above is 7.08 pound-inches/0.354 inches=20 pounds.

Accordingly, in view of the above, it may be seen that the leaf spring 1270 and the expandable member 1230 cooperate to provide a substantially constant distraction force to the first plate 1210 or 1220 at various points along the range of motion of the first plate 1210 or 1220. It will be apparent to those of skill in the art that the specific dimensions and force measurements shown above are only exemplary and that the same principles may be embodied in a device that is larger or smaller, that is configured to apply a force of greater or lesser magnitude, etc.

Figure 12D:
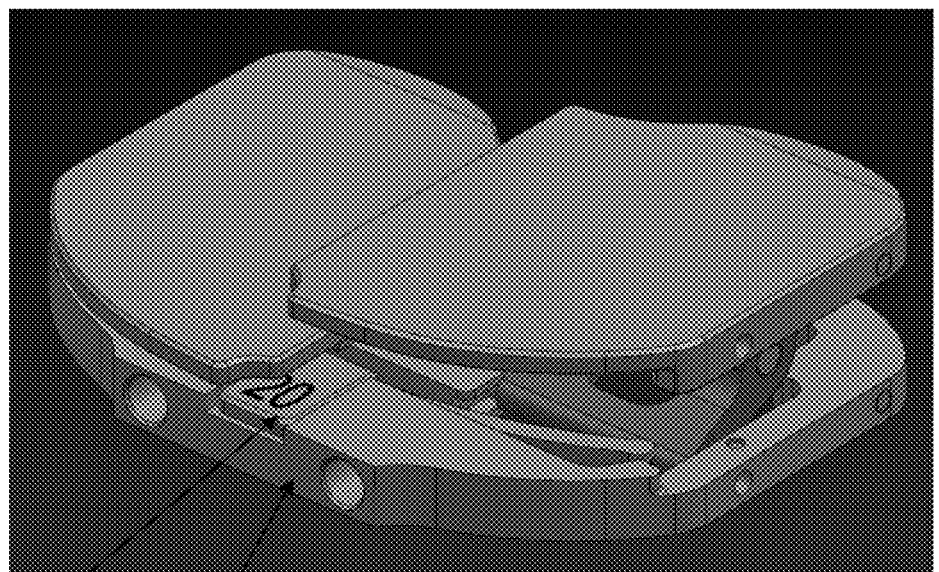
Figure 12E:
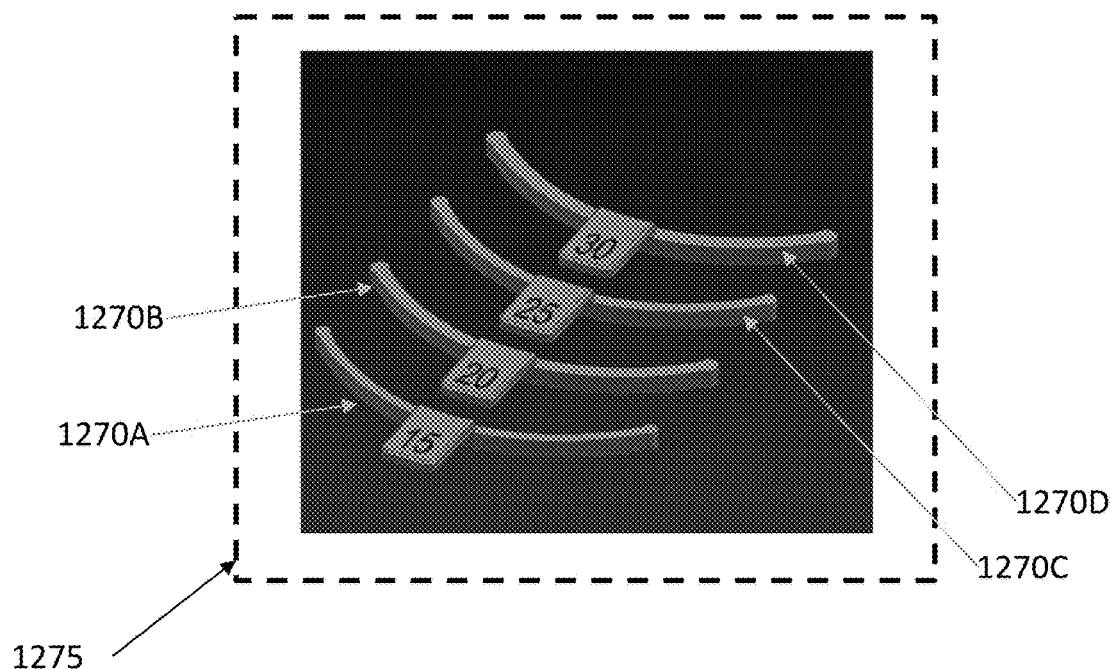

FIGS. 12D-12F show variants of the fifth exemplary ligament balancing device 1200, which are configured to allow the stiffness of the leaf spring 1270 to be adjusted intraoperatively, thereby allowing the distraction force applied by the device 1200 to be adjusted. FIGS. 12D-12E show a first variant device 1201, in which a kit 1275 including at least two leaf springs 1270A, 1270B, etc. is provided. In some embodiments, each of the at least two leaf springs 1270A, 1270B, etc. has distinct mechanical properties (e.g., different cross-sections, different materials, different heat treatment, etc.) which combine to cause the at least two leaf springs 1270A, 1270B, etc. to have different stiffnesses from one another. In some embodiments, the device 1201 is configured so as to allow one leaf spring (e.g., the leaf spring 1270A) to be interchanged with another leaf spring (e.g., the leaf spring 1270B). In some embodiments, because of the difference of stiffness between two leaf springs within the kit 1275, the distraction force applied by the device 1201 differs depending on which specific one of the leaf springs within the kit 1275 is used. For example, in some embodiments, the kit 1275 includes a first leaf spring 1270A configured to cause the device to apply a distraction force of 15 pounds to the joint, a second leaf spring 1270B configured to cause the device to apply a distraction force of 20 pounds to the joint, a third leaf spring 1270C configured to cause the device to apply a distraction force of 25 pounds to the joint, and a fourth leaf spring 1270D configured to cause the device to apply a distraction force of 30 pounds to the joint. In some embodiments, the leaf springs within the kit 1275 are most easily interchanged when the device 1201 is not placed into a patient's joint, such that in the absence of compressive force from the joint, the first plates 1210, 1220 spaced away from the second plate 1250, thereby allowing for easy access to the one of the leaf springs within the kit 1275 that is currently positioned within the device 1201.

FIG. 12F shows a second variant device 1202. In the embodiment shown in FIG. 12F, the device 1202 includes a mechanism 1280 that is operable to increase or decrease the pre-load of the leaf spring 1270, thereby increasing or decreasing the distraction force to be applied by the device 1202. In some embodiments, the mechanism 1280 includes a set screw. In other embodiments, the mechanism 1280 includes an operable lever featuring a cam portion contacting the leaf spring 1270, which, depending on the section of the cam portion in contact with the leaf spring 1270, increases or decreases the pre-load of the leaf spring 1270 and, thereby, increases or decreases the distraction force to be applied by the device 1202. In some embodiments, adjustment of the device 1202 can be performed in situ while the device 1201 is positioned within a patient's joint. In use, the device 1202 allows the surgeon to tailor the distraction force based on patient characteristics (e.g., BMI, size, or ligament stiffness/condition) or based on surgeon preferences as an attempt to personalize the distraction force (as an input) based on which the joint gaps would be measured (as an output).

In some embodiments, both the device 1201 and the device 1202 allow a user (e.g., a surgeon) to personalize the distraction force depending on the patient. In some embodiments, the device 1201 and the device 1202 can be adapted into compartment-specific versions similar to the modules 1001 and 1002 shown in FIG. 10A. In such embodiments, rather than offering the modules 1001, 1002 under different stiffness levels (e.g., low, medium, high) to provide customization options to a user, each compartment-specific device can be tuned to a singular distraction force at the time of the surgery without requiring a kit. In some embodiments, such a device allows for fine-tuning of the distraction force between the medial and lateral compartment, as well as for different angles of flexion (whether specifically in the context of total knee arthroplasty or more generally in the context of any bicondylar joint) or for fine tuning of the distraction force for a given compartment as well as different angles of flexion (e.g., for a partial/unicompartmental knee arthroplasty or for surgery on a unicondylar joint). In some embodiments, the device 1202 including the adjustment mechanism 1280 allows for a continuous adjustment of force through an available range, rather than providing discrete incremental levels (e.g., low, medium, high) of distraction force.

Both the fourth and fifth exemplary ligament balancing devices 1100, 1200 are presented herein as potential modes of realization. Based on these two descriptions, it will be apparent to those of skill in the art that the mechanical actuator of such a device can be understood in more general terms as the combination of two antagonist sub-mechanisms, i.e., sub-mechanisms that provide an axial distraction force that fluctuate in opposite directions of the direction of travel of the device from one another, wherein the two sub-mechanisms are designed in such a way that an increase in the force induced by one of the sub-mechanisms due to movement of the device is compensated for by a corresponding decrease in the force induced by the other of the sub-mechanisms due to the same movement, thereby maintaining a substantially constant distraction force applied to the joint regardless of the distance between opposing plates of the device. In some embodiments, the actuation mechanisms are located between at least two plates intended to contact opposing bones of a given joint. As used herein, "sub-mechanism" should be understood broadly as a mechanism that has the capacity to absorb, store and release energy through a change in shape (e.g., spring) or a change of a mechanical variable (e.g., moment arm).

In some embodiments, wherein a mechanical actuator is located inside a perimeter defined by the first plate or the second plate and by the opposing bony structures of the joint, the proposed device could be described as intraarticular and intracapsular. An intraarticular device possesses advantages such as allowing for the possibility of closing the arthrotomy of a joint in order to better reflect a physiological kinematic of the joint during the manipulation of the joint, as well allowing for the reduction of the footprint of the device.

The exemplary embodiments described above incorporate compression springs and leaf springs. However, it will be apparent to those of skill in the art that the sub-mechanisms described herein can also be achieved by any type of spring (e.g., compression springs, leaf springs, extension springs, torsion springs, Belleville springs, drawbar springs, volute springs, garter springs, etc.), manufactured from diverse materials (e.g., metals such as steel or aluminum, elastomeric materials, etc.), and configured in any form and fit to achieve the intended distraction force.

In some embodiments, the exemplary ligament balancing devices described above are configured for use in the management of the soft tissue during a total knee arthroplasty type of procedure, wherein the device can be intraarticularly placed into the prepared knee joint and apply a similar distraction force on both the lateral compartment and the medial compartment so the surgeon can properly assess the joint space as well as the relative joint alignment under constant distraction force regardless of the joint gap/space of each compartment. In some embodiments, due to the versatility of the disclosed ligament balancing devices, such devices can be provided as part of a conventional mechanical instrumentation set or in combination with a navigation system. Similarly, in some embodiments, the exemplary balancing devices described above can be used at different stages of the procedure regardless of the surgical technique.

According to one example of usage, an exemplary ligament balancing device (e.g., the device 400, 600, 700, 800, 1000, 1100, 1200, 1201, or 1202) is used in conjunction with a navigation system, such as the navigation system commercialized by Exactech, Inc. of Gainesville, Florida under the trade name EXACTECHGPS. In some embodiments, a navigation system includes a display unit combining an infrared charge-coupled device (CCD) camera and a touchscreen tablet intended to be located in the sterile field (under a sterile drape) and directly accessible by the surgeon during the surgery, as well as a set of trackers configured to be rigidly attached to a patient's bone. In some embodiments, the CCD camera is configured to define the 3D position and orientation of the trackers, surgical instruments, and a system-specific probe within 6 degrees of freedom during the acquisition of anatomical landmarks. In some embodiments, the navigation system includes an intraoperative application configured to compute the acquired data to establish a surgical plan and to provide real-time visual guidance to execute the surgical plan. In some embodiments, the navigation system encompasses a navigated mechanical instrument intended to receive a tracker and facilitate execution of the surgical plan.

Figure 13A:
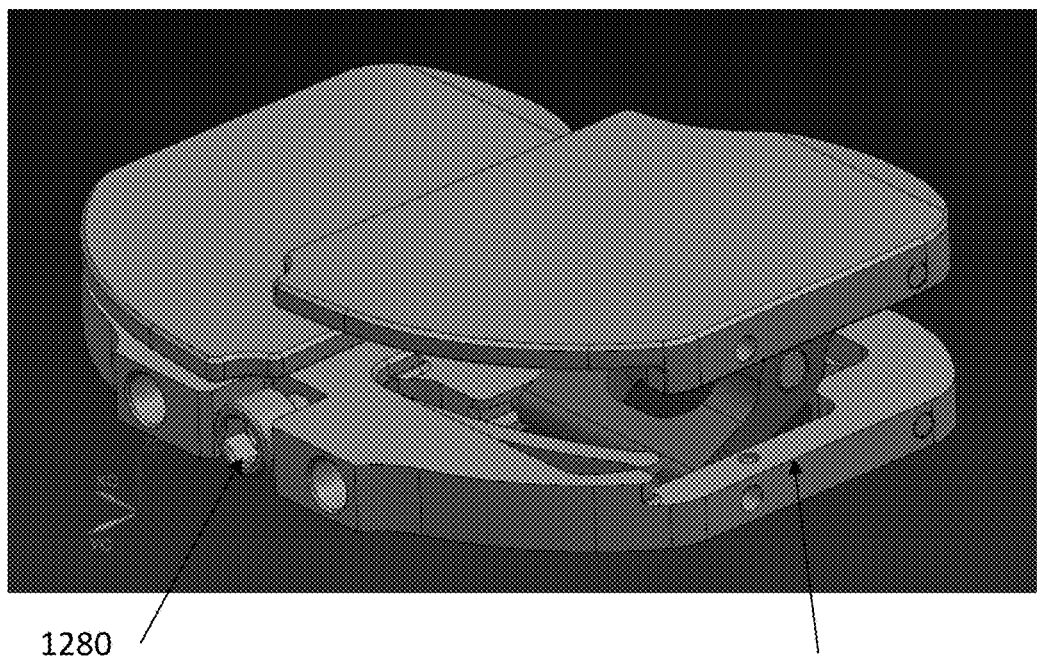
FIG. 13A shows an exemplary ligament balancing device and an exemplary compression handle.
Figure 13A:
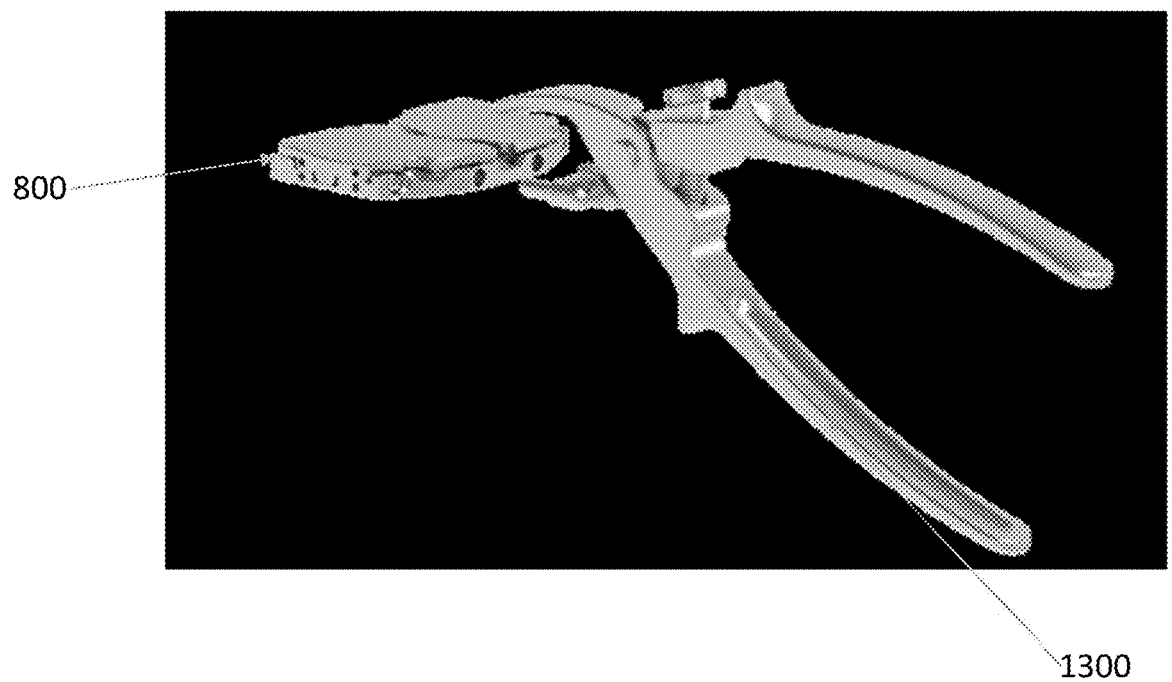
Figure 13B:
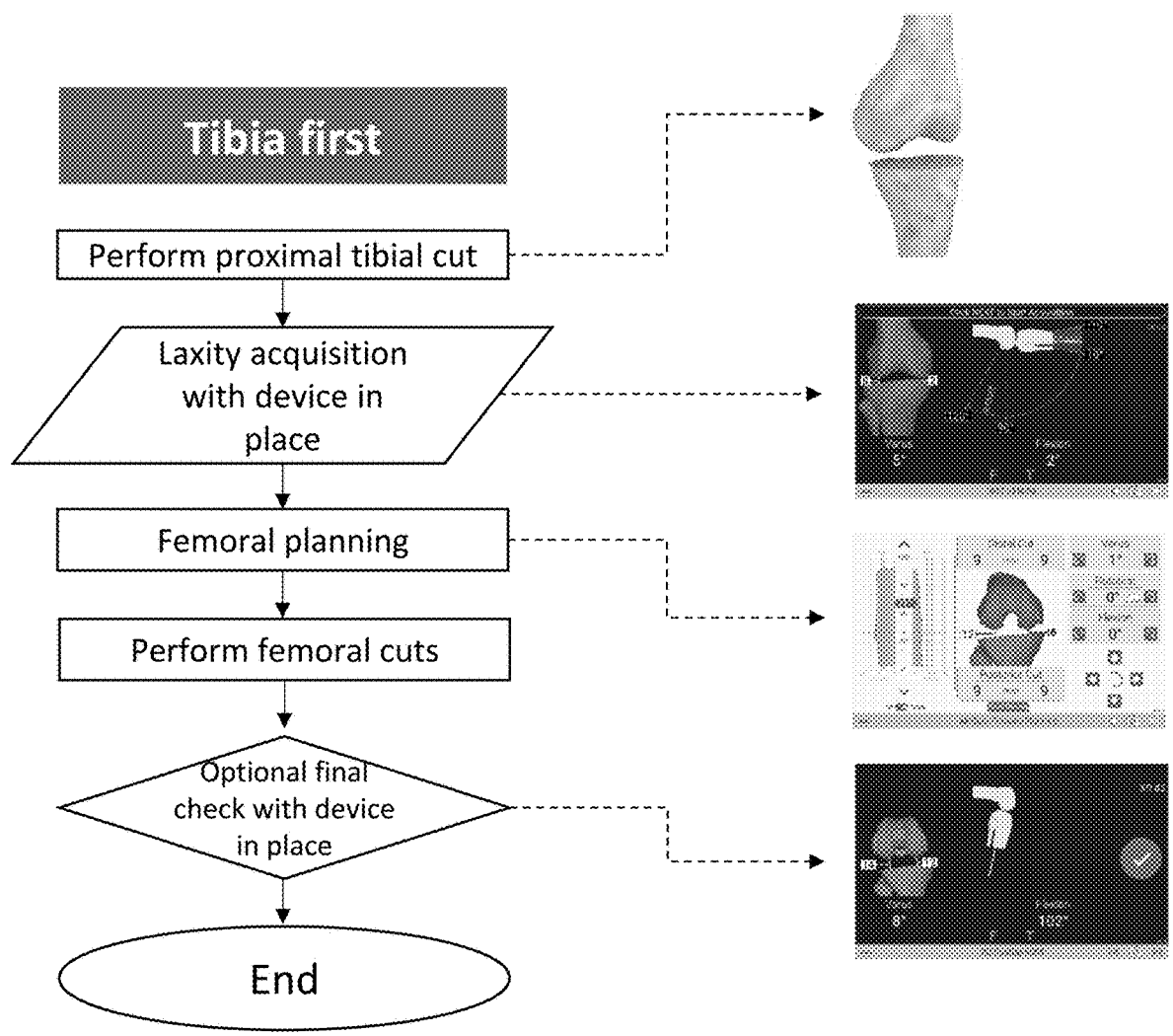
FIG. 13B shows a workflow for an exemplary "tibia first" technique for total knee arthroplasty.

In some embodiments, an exemplary ligament balancing device (e.g., the device 400, 600, 700, 800, 1000, 1100, 1200, 1201, or 1202) is used in connection with a surgical technique known as "tibia first". FIG. 13A shows an exemplary ligament balancing device as coupled to an exemplary compression handle 1300 for use in a tibia first technique. FIG. 13B shows the overall surgical workflow of a tibia first technique. In such a technique, the proximal tibial cut is first performed and potential osteophytes around the margins of the native tibia and/or femur are removed. In some embodiments, performance of the proximal tibial cut results in a joint space compatible with the overall dimensions of the exemplary ligament balancing devices in terms of both the transverse dimensions (more or less defined by the perimeter of the proximal tibial cut) and the thickness (defined by the distance between the proximal tibial cut surface and the native femur. Next, in some embodiments, the exemplary ligament balancing device is attached to the compression handle 1300, as shown in FIG. 13A, and is compressed so as to provide the smallest overall thickness of the ligament balancing device (e.g., the lowest distance between the first plate and the second plate). In some embodiments, once compressed, the exemplary ligament balancing device is placed into the joint space and the compression handle is subsequently removed from the ligament balancing device, which results into the application of an axial distraction force to both the medial compartment and the lateral compartment of the joint (e.g., through the medial actuation mechanism located between the medial first plate in contact with the medial condyle of the native femur and the second plate, and through the lateral actuation mechanism located between the lateral first plate in contact with the lateral condyle of the native femur and the second plate, respectively). In some embodiments, at this stage, the surgeon can (1) bring the leg in extension to later balance the knee in extension by recording the joint spaces in extension, and/or (2) bring the leg in flexion to later balance the knee in flexion by recording the joint spaces in flexion, and/or (3) manipulate the leg from extension to flexion to later balance the knee through the arc of motion by recording the joint spaces from extension to flexion, and/or (4) manipulate the leg from flexion to extension to later balance the knee through the arc of motion by recording the joint spaces from flexion to extension. In some embodiments, for any of these options, the joint spaces at specific angles of flexion or through a range of angles of flexion are recorded by the navigation platform as the tracking of the femoral referential (associated with the femoral tracker) into the tibial referential (associated with the tibial tracker). In some embodiments, for options (3) and (4), several methods of handling of the leg are possible, such as placing one hand on the posterior aspect of the femur with the tibia in flexion to prevent the weight of the femur from affecting the measurements, and placing the other hand at the level of the distal tibia or heel with care not to apply a *varus*/valgus or internal/external rotation moment to the knee joint, while slowly moving the leg from extension to flexion or from flexion to extension. In some embodiments, based on the recorded joint spaces as well as other inputs (e.g., alignment of the leg, size of the knee components, method of alignment), the navigation system computes and displays a femoral plan encompassing the cut parameters, which the surgeon can validate as-is or fine-tune as desired. In some embodiments, once the femoral plan has been confirmed, the femoral cuts are performed under guidance of the navigation system.

In some embodiments, a last optional step includes performing a trial reduction where a trial femoral component is placed onto the prepared femur and the ligament balancing device is placed into the joint space a second time. In some embodiments, by manipulating the leg through the arc of motion, this step offers the possibility of checking the joint gaps and alignment when an axial distraction force is applied to both the medial compartment and the lateral compartment in the same manner as described above.

Figure 14A:
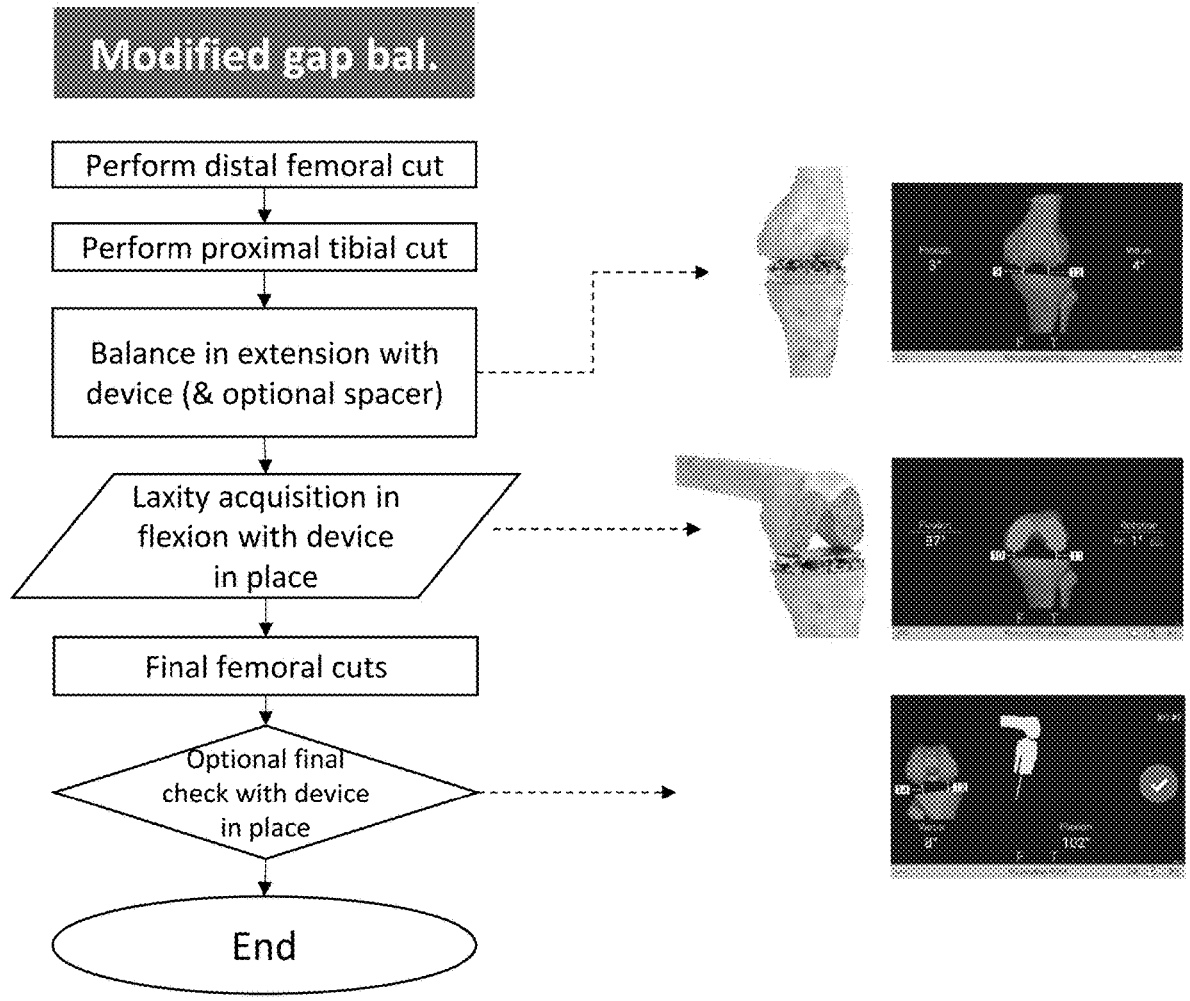
FIG. 14A shows a workflow for an exemplary "modified gap balancing" technique for total knee arthroplasty.
Figure 14B:
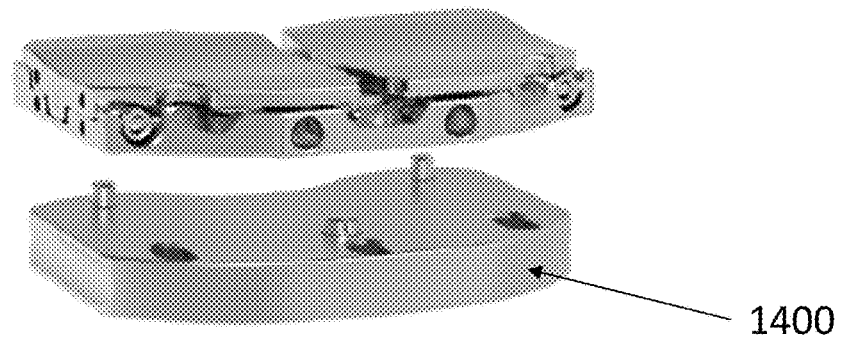
FIG. 14B shows an exemplary ligament balancing device and an exemplary spacer provided for use during a technique such as the technique shown in FIG. 14A.

In some embodiments, an exemplary ligament balancing device (e.g., the device 400, 600, 700, 800, 1000, 1100, 1200, 1201, or 1202) is used in connection with a surgical technique known as "modified gap balancing". FIG. 14A describes the overall surgical workflow of a "modified gap balancing" technique. In some embodiments, in a "modified gap balancing" technique, the distal femoral cut is performed first, and the proximal tibial cut is performed second. In some embodiments, in a "modified gap balancing" technique, the proximal tibial cut is performed first and the distal femoral cut is performed second. In some embodiments, performance of both cuts, osteophytes around the margins of the native tibia and/or femur are removed, resulting in a joint space compatible with the overall dimensions of the ligament balancing device in terms of both the transverse dimensions (generally defined by the perimeter of the proximal tibial cut) and thickness (defined by the distance between the proximal tibial cut surface and the distal femoral cut surface). In some embodiments, depending of the gap between the two bone cuts, the axial thickness of the ligament balancing device can be augmented by a spacer 1400 (see FIG. 14B). In some embodiments, the spacer 1400 is positioned distally to the second plate. In some embodiments, the spacer 1400 is positioned proximally to the proximal plate(s). In some embodiments, the ligament balancing device is attached to a compression handle and is compressed to produce the smallest overall thickness of the ligament balancing device (e.g., the lowest distance between the proximal plate(s) and the distal plate). In some embodiments, once assembled to a compression handle (e.g., as shown above in FIG. 13A) and, optionally, to one or more spacers as described above, the compressed ligament balancing device is placed into the joint space while the joint is positioned in extension, and the compression handle is subsequently removed from the ligament balancing device. In some embodiments, such positioning of the exemplary ligament balancing device results in the application of an axial distraction force to both the medial compartment and the lateral compartment of the knee joint. In some embodiments, at this stage, the surgeon assesses the knee in extension by checking the alignment of the overall leg as well as the values of the medial and lateral gaps as displayed on the screen of the navigation system. In some embodiments, based on this information, the surgeon may elect to perform ligament release(s) in order to optimize the alignment. In some embodiments, once proper balance in extension is achieved, the leg is brought into flexion for the assessment of the balance in flexion. In some embodiments, it is necessary to remove the spacer 1400 (if in use to compensate for the thickness of the distal femoral cut) before balancing in flexion because when the knee is in flexion, the proximal plates are in contact with the native posterior condyles of the femur. At this stage, balancing can be performed (1) in a static manner (e.g., at a defined angle associated with the leg being in flexion, typically between 80° and 100° of flexion) or (2) a dynamic manner by bringing the leg from mid-flexion (required to ensure the contact between the still native portion of the femur and the proximal plates) to high flexion or from high flexion to mid-flexion. In some embodiments, the joint spaces at specific angles of flexion or through a range of angles of flexion are recorded by the navigation platform by tracking of the femoral referential (associated with the femoral tracker) and the tibial referential (associated with the tibial tracker). In some embodiments, based on the recorded joint spaces as well as other inputs (e.g., size of the knee components, method of alignment), the navigation system computes and displays a femoral plan encompassing the cut parameters for the final preparation of the femur, which the surgeon can validate as-is or can fine-tune. In some embodiments, once the plan has been confirmed, the final femoral cuts are performed under guidance of the navigation system.

In some embodiments, a last optional step includes performing trial reduction where a trial femoral component is placed onto the prepared femur and the ligament balancing device is placed into the joint space. In some embodiments, by manipulating the leg through the arc of motion, this allows the surgeon to verify the joint gaps and alignment when an axial distraction force is applied to both the medial compartment and the lateral compartment in the same manner as described above.

Figure 15:
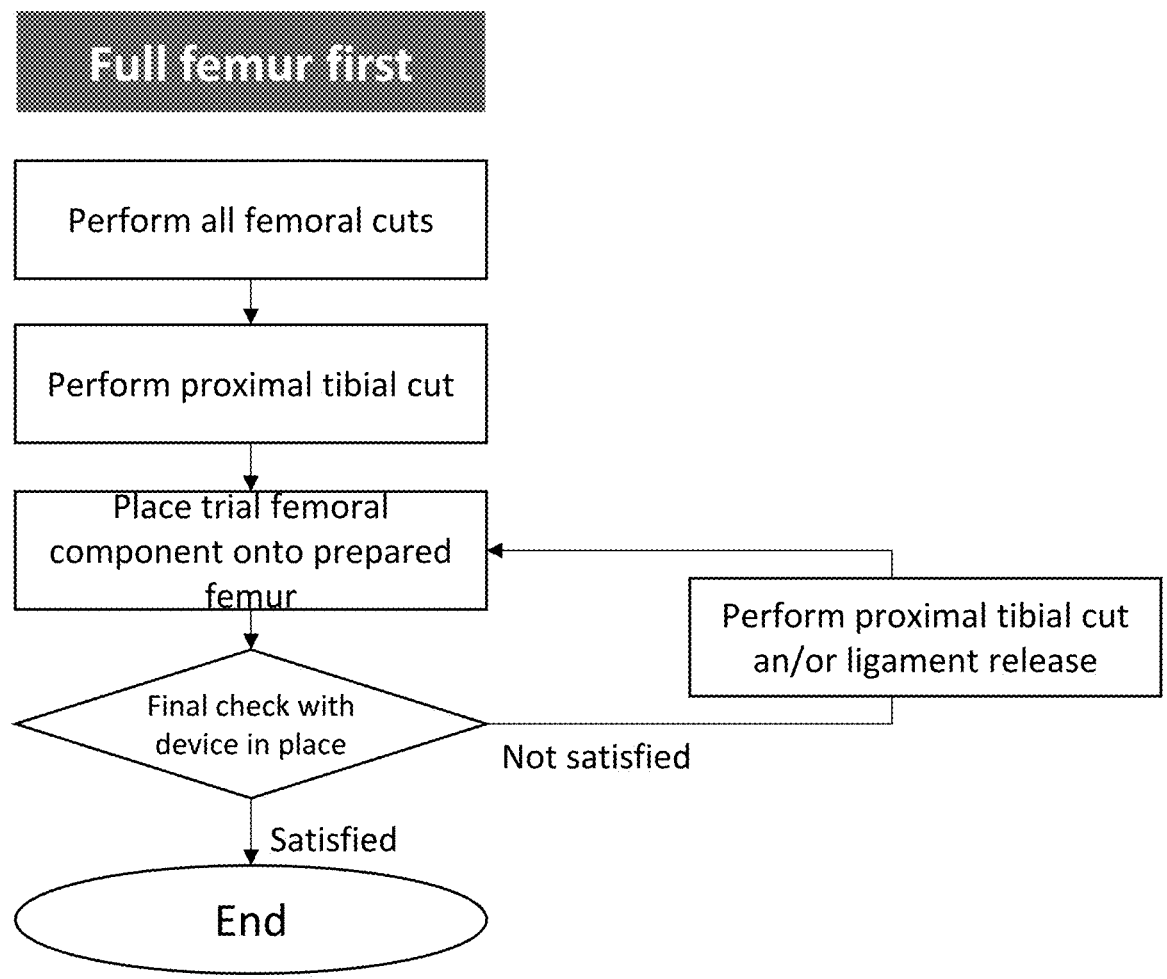
FIG. 15 shows an exemplary "full femur first" technique for total knee arthroplasty.

In some embodiments, an exemplary ligament balancing device (e.g., the device 400, 600, 700, 800, 1000, 1100, 1200, 1201, or 1202) is used in connection with a surgical technique known as "femur first". FIG. 15 describes the overall surgical workflow of a "femur first" technique. In some embodiments of a "femur first" technique, all femoral cuts are performed first (e.g., as opposed to the technique shown in FIG. 14, in which only the distal femoral cut is performed first), and the proximal tibial cut is performed second. In some embodiments of a "femur first" technique, the proximal tibial cut is performed first and all femoral cuts are performed second. In some embodiments, following performance of all femoral cuts and the proximal tibial cut, potential osteophytes around the margins of the native tibia and/or femur are removed. In some embodiments, following removal of osteophytes, a trial femoral component is placed on the prepared femur, thereby producing a joint space that is compatible with the overall dimensions of an exemplary ligament balancing device in terms of both the transverse dimensions (generally defined by the perimeter of the proximal tibial cut) and the thickness (defined by the distance between the proximal tibial cut and the trial femoral component). Next, in some embodiments, the ligament balancing device is attached to a compression handle (e.g., as shown above in FIG. 13A) and is compressed to so as to produce the smallest overall thickness of the ligament balancing device (e.g., the lowest distance between the proximal plate(s) and the distal plate). In some embodiments, the compressed ligament balancing device is placed into the joint space and the compression handle is subsequently removed from the ligament balancing device, resulting in the application of an axial distraction force to both the medial compartment and the lateral compartment in the manner described above. In some embodiments, at this point, the surgeon manipulates the leg through the arc of flexion to check the balance and the alignment of the knee by recording these data through the navigation system. In some embodiments, depending on the measured balance and alignment, the surgeon may or may not be satisfied. In some embodiments, if the surgeon is satisfied, the surgeon next implants the final implant components. In some embodiments, if the surgeon is not satisfied, the surgeon may elect to perform subsequent surgical change(s) such as ligament release(s) or bone cut(s) to improve the balance and/or the alignment of the knee joint, and may then reassess the balance and alignment of the knee by manipulating the leg through the arc of flexion after the said surgical change(s).

In some embodiments, an exemplary ligament balancing device (e.g., the device 400, 600, 700, 800, 1000, 1100, 1200, 1201, or 1202) is used in conjunction with conventional mechanical instrumentation (e.g., in the absence of a navigation system) as a balancer to assess the symmetry of the gaps (e.g., the difference between the medial gap and the lateral gap). In some embodiments, such an assessment can be performed with any of the previously described surgical techniques.

Certain aspects of the exemplary embodiments described above with reference to FIGS. 4-15 have been described with specific reference to the characteristics of a knee joint. However, the principles embodied by the exemplary embodiments are also applicable to balancing devices adapted for use in other joints.

Figure 16:
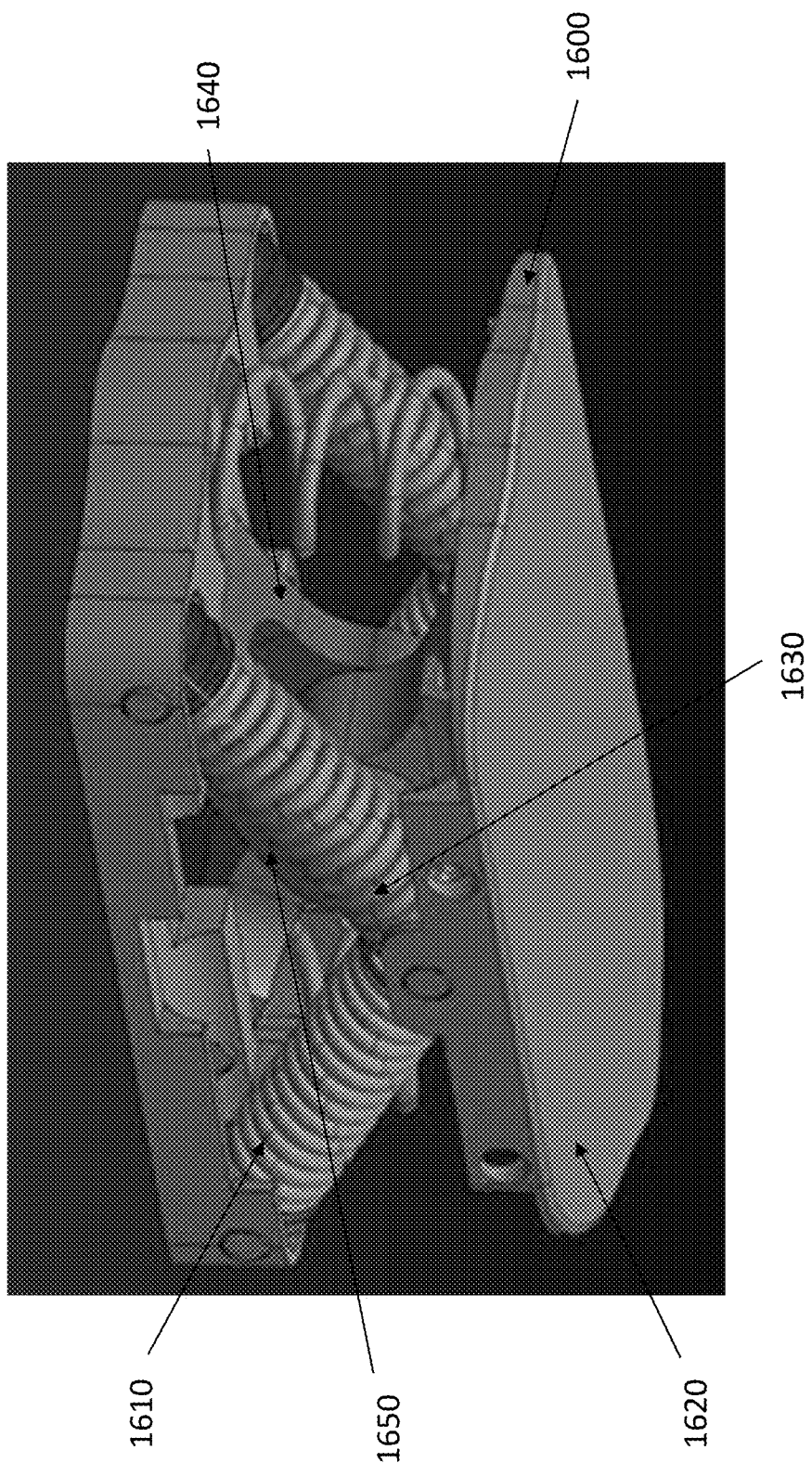
FIG. 16 shows an exemplary device as adapted for use in total ankle arthroplasty.

FIG. 16 shows a perspective view of a device 1600 adapted for use in total ankle arthroplasty. In some embodiments, the device 1600 includes a first plate (e.g., a proximal plate) 1310 that is configured (e.g., sized and shaped) to engage the distal end of a patient's tibia. In some embodiments, the first plate 1610 is configured to engage a distal cut surface of the patient's native tibia. In some embodiments, the device 1600 includes a second plate (e.g., a distal plate) 1620 that is configured (e.g., sized and shaped) to engage the patient's native talus. In some embodiments, the device 1600 includes an expandable member 1630 positioned between the first plate 1610 and the second plate 1620 and operable to apply a distraction force between the first plate 1610 and the distal plate 1620 in accordance with any of the exemplary embodiments described herein. In the embodiment shown in FIG. 16, the expandable member 1630 includes a mechanical actuator (e.g., an arrangement including one or more springs). In some embodiments, the mechanical actuator is configured to provide a constant or quasi-constant force across the range of motion of the device 1600. In some embodiments, the device 1600 includes first and second stability mechanisms 1640, 1650 positioned between the first plate 1610 and the second plate 1620 and configured to impart improved stability (e.g., rigidity) to the device 1600 in a manner such as those described above. In some embodiments, the device 1600 includes one first plate 1610 and at least two of the second plate 1620. In some embodiments, the device includes at least two of the expandable member 1630 and each of the at least two second plates 1620 is associated with a corresponding one of the at least two expandable members 1630.

In some embodiments, the device 1600 is adapted for use in a total ankle arthroplasty process for repair of a patient's ankle joint involving the steps of (1) cutting the distal end of the patient's native tibia to produce a cut tibial surface, (2) positioning the device 1600 between the cut tibial surface and the patient's native talus, (3) moving the ankle joint through a range of motion while recording data to characterize laxities of the patient's ankle ligaments, and (4) planning cuts to the patient's talus and/or release of surrounding soft tissue based on the previously acquired laxities of the patient's ankle ligaments, together with other factors such as the overall alignment of the ankle joint, the position and/or orientation of the cut to the talus based on anatomical considerations or patient-specific considerations (e.g., the presence of a cyst near the ankle joint, the presence of previously implanted surgical implants), etc.

In some embodiments, the device 1600 is adapted for use in a total ankle arthroplasty process for repair of a patient's ankle joint involving the steps of (1) cutting the proximal end of the patient's native talus to produce a cut talar surface, (2) positioning the device 1600 between the cut talar surface and the patient's native tibia, (3) moving the ankle joint through a range of motion while recording data to characterize laxities of the patient's ankle ligaments, and (4) planning cuts to the patient's tibia and/or release of the surrounding soft tissue based on the previously acquired laxities of the patient's ankle ligaments, together with other factors such as the overall alignment of the ankle joint, the position and/or orientation of the cut to the talus based on anatomical considerations or patient-specific considerations (e.g., the presence of a cyst near the ankle joint, the presence of previously implanted surgical implants), etc.

Figure 17A:
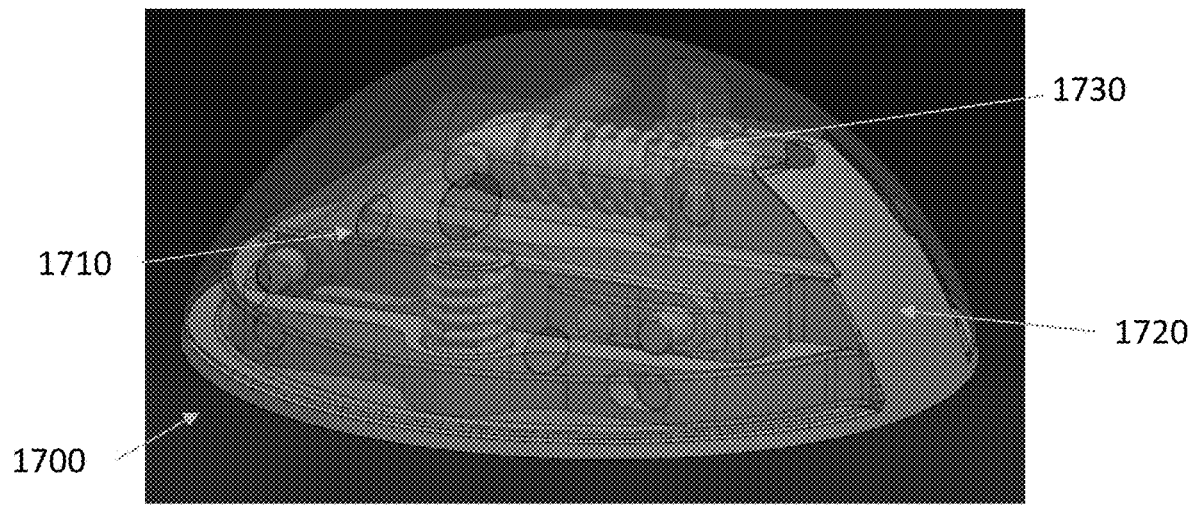
FIGS. 17A and 17B show an exemplary device as adapted for use in anatomical total shoulder arthroplasty.
Figure 17B:
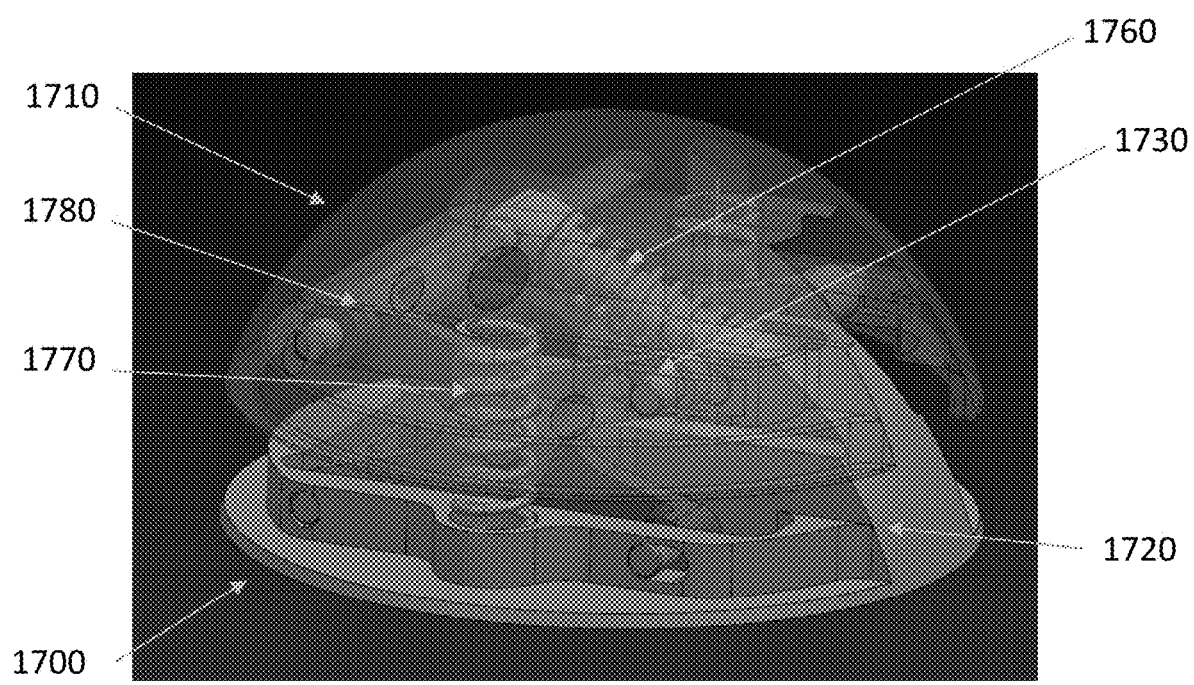

FIGS. 17A and 17B shows first and second perspective views of a device 1700 adapted for use in anatomical total shoulder arthroplasty ("aTSA"). In the first perspective view of FIG. 17A, the device 1700 is shown in a collapsed position. In the second perspective view of FIG. 17B, the device 1700 is shown in an expanded position. In FIGS. 17A and 17B, certain elements of the device 1700 are rendered in a partially transparent manner in order to enhance visibility of other elements of the device 1700. In some embodiments, the device 1700 includes a first plate (e.g., a medial plate) 1710 that is configured (e.g., sized and shaped, such as curved) to engage a patient's native glenoid cavity or a glenoid implant positioned on the patient's prepared glenoid. In some embodiments, the device 1700 includes a second plate (e.g., a lateral plate) 1720 that is configured (e.g., sized and shaped) to engage a cut surface of the patient's proximal humerus and/or a surface of a humeral prosthesis. In some embodiments, the device 1700 includes an expandable member 1730 positioned between the first plate 1710 and the second plate 1720 and operable to apply a distraction force between the first plate 1710 and the second plate 1720 in accordance with any of the exemplary embodiments described herein. In some embodiments, such as shown in FIGS. 17A and 17B, the expandable member 1730 is at least partially embedded within the first plate 1710. In the embodiment shown in FIGS. 17A and 17B, the expandable member 1730 includes a mechanical actuator. In some embodiments, the expandable member 1730 includes two antagonist force sub-mechanisms 1760, 1770. In some embodiments, the device 1700 includes one or more stability mechanisms 1780 positioned between the first plate 1710 and the second plate 1720 and configured to impart improved stability (e.g., rigidity) to the device 1700 in a manner such as those described above. In some embodiments, the device 1700 is provided in a monoblock arrangement in which the first plate 1710 is linked through sub-components of the actuation mechanism (e.g., the combination of the expandable member 1730 and the stability mechanisms 1780) to the second plate 1720. As used herein, the term "monoblock" refers to a device that is a single, unitary, non-modular whole that is not configured to be adjusted with different interchangeable portions thereof. In some such embodiments, the device 1700 is provided as a kit including versions of the device 1700 having different configurations of size and shape of the first plate 1710. In some embodiments, the device 1700 is provided as a modular device including an expansion sub-device (e.g., encompassing the expandable member 1730 and the stability mechanisms 1780) that is fixed to the second plate 1720 (e.g., to produce a plate sub-assembly), and with the first plate 1710 that is an interchangeable trial element that is directly connectable with the expansion sub-device. In some such embodiments, the device 1700 is provided as a kit including the first plate 1710 that is a trial element in different configurations of size and shape.

In some embodiments, the device 1700 is adapted for use in an aTSA process for repair of a patient's shoulder joint involving the steps of (1) cutting the proximal end of the patient's native humerus to produce a cut humeral surface, (2) placing a humeral component trial or implant on the cut humeral surface, (3) positioning the device 1700 between the humeral component trial or implant and the patient's native or prepared glenoid portion of the scapula, (4) moving the shoulder joint through a range of motion while recording data to characterize laxities of the patient's shoulder ligaments, and (5) (a) planning the preparation of the glenoid portion of the patient's native scapula (if step 3 was performed on the patient's native glenoid portion of the scapula), or (b) selecting a prosthesis based on the laxities of the patient's shoulder ligaments (if step 3 was performed on the patient's prepared glenoid portion of the scapula).

Figure 18:
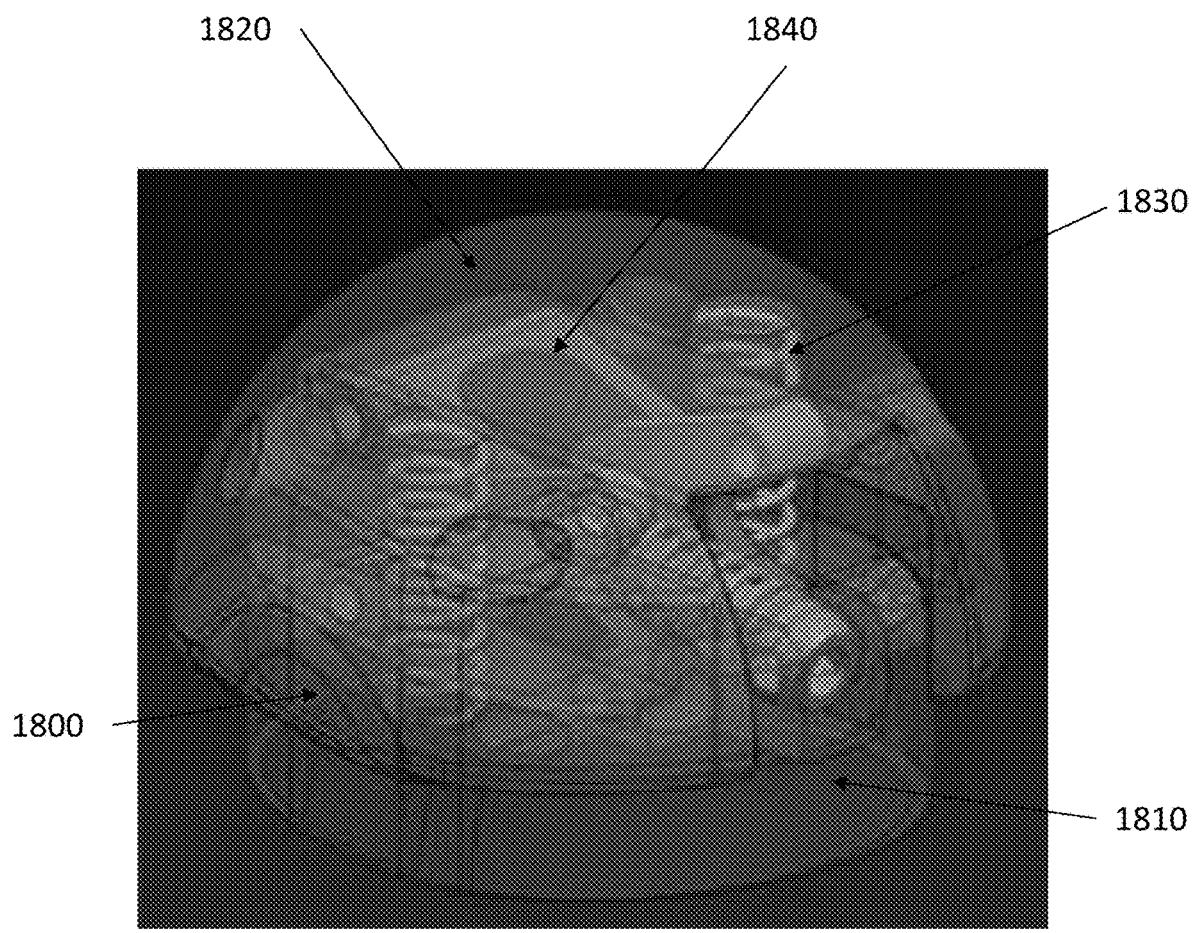
FIG. 18 shows an exemplary device as adapted for use in reverse total shoulder arthroplasty.

FIG. 18 shows a partially transparent perspective view of a device 1800 adapted for use in reverse total shoulder arthroplasty ("rTSA"). In some embodiments, the device 1800 includes a first plate (e.g., a medial plate) 1810 that is configured (e.g., sized and shape) to engage a glenoid plate of a scapular side of a reverse shoulder prosthesis. In some embodiments, the device 1800 includes a second plate (e.g., a lateral plate) 1820 that is configured (e.g., sized and shaped) to engage a humeral liner (or trial humeral liner) of a humeral side of a reverse shoulder prosthesis. The first and second plates 1810, 1820 should be understood to be substantially similar to the various first and second plates described herein. In some embodiments, the device 1800 includes an expandable member 1830 positioned between the first plate 1810 and the second plate 1820 and operable to apply a distraction force between the first plate 1810 and the second plate 1820 in accordance with any of the exemplary embodiments described herein. In some embodiments, such as the embodiment shown in FIG. 16, the expandable member 1830 includes a mechanical actuator (e.g., an arrangement including one or more springs). In some embodiments, the mechanical actuator is configured to provide a constant or quasi-constant force across the range of motion of the device 1800. In some embodiments, such as shown in FIG. 18, the expandable member 1830 is at least partially embedded within the second plate 1820. In some embodiments, the device 1800 includes a stability mechanism 1840 that is positioned between the first plate 1810 and the second plate 1820 and is configured to impart improved stability (e.g., rigidity) to the device 1800 in a manner such as those described above. Although only one stability mechanism 1840 is visible in FIG. 16, in some embodiments, the device 1800 includes more than one stability mechanism of the stability mechanism 1840 (e.g., two of the stability mechanisms 1840).

In some embodiments, the device 1800 is provided as a monoblock device in which the first plate 1810 is linked through subcomponents of the actuation mechanism (e.g., the expandable member 1830) to the second plate 1820. In some such embodiments, the device 1800 is provided as part of a kit including different ones of the device 1800 having different configurations of size and shape of the second plate 1820. In some embodiments, the device 1800 is provided as a modular device including an expansion sub-device (e.g., including the expandable member 1830 and the stability mechanism 1840) that fixed to with the first plate 1810 (e.g., to produce a plate sub-assembly), and with the second plate 1820 that is an interchangeable trial element directly connectable with the expansion sub-device. In some such embodiments, the device 1800 is provided as part of a kit that includes different ones of the second plate 1820 that have different configurations in terms of size and shape.

In some embodiments, the device 1800 is adapted for use in an rTSA process for repair of a patient's shoulder joint involving the steps of (1) preparing the patient's scapula and positioning a glenoid plate on the patient's scapula, (2) preparing the patient's humerus and positioning a humeral tray and trial humeral liner on the patient's humerus, (3) positioning the device 1800 between the glenoid plate and the trial humeral liner, (4) moving the shoulder joint through a range of motion while recording data to characterize laxities of the patient's shoulder ligaments, and (5) selecting a humeral liner and/or a humeral tray based on the laxities of the patient's shoulder ligaments.

It will be apparent to those of skill in the art that aspects of the embodiments described above can be combined with one another so that a surgeon can personalize the ligament balancing device (e.g., a medial module with high stiffness level, a large size, and a concave proximal femoral plate linked with a lateral module with a medium stiffness level, a small size, and a convex proximal femoral plate) depending on the needs of a given patient.

In some embodiments, an exemplary ligament balancing device is configured to maintain a constant or quasi-constant distraction force without including or being coupled to any type of active control arrangement or mechanism. In some embodiments, an exemplary ligament balancing device is configured to maintain a constant or quasi-constant distraction force without including or being coupled to any type of external control mechanism. In some embodiments, an exemplary ligament balancing device is configured to maintain a constant or quasi-constant distraction force without being coupled to any type of external device. In some embodiments, an exemplary ligament balancing device is a self-contained device that is configured to maintain a constant or quasi-constant distraction force without including or being coupled to any type of external control mechanism. In some embodiments, an exemplary ligament balancing device is configured to maintain a constant or quasi-constant distraction force without including any type of powered (e.g., electrically powered) element. In some embodiments, an exemplary ligament balancing device is configured (e.g., sized and shaped) to be positioned intra-articularly and/or intracapsularly within a joint (e.g., to be positioned entirely within the joint space in a manner such that the tissue can be closed with the exemplary ligament balancing device in place. In some embodiments, an exemplary ligament balancing devices includes a mechanical actuation mechanism that is positioned entirely within the perimeter of a first plate and the perimeter of a second plate so as to enable the exemplary ligament balancing device to be positioned intra-articularly and/or intracapsularly within a joint.

In some embodiments, an exemplary ligament balancing device includes a motor (or motors) and a transmission (or transmissions), which are used to control the expansion of the expandable members. In some embodiments, feedback from torque sensors allows the motor controller to adjust motor output (e.g., speed, displacement, torque, or direction) to maintain a constant or quasi-constant force.

In some embodiments, an exemplary ligament balancing device includes a linear actuator (or actuators) that is used to control the expansion of the expandable members. In some embodiments, feedback from force sensors allows the actuator controller to adjust actuator output (e.g. speed, displacement, torque, or direction), maintaining a constant or quasi-constant force.

In some embodiments, the expandable members include thermomechanical actuators (e.g. a shape memory alloy, a thermal bimorph, a heated spring, etc.) that are heated and cooled to maintain a constant or quasi-constant force.

Figure 19A:
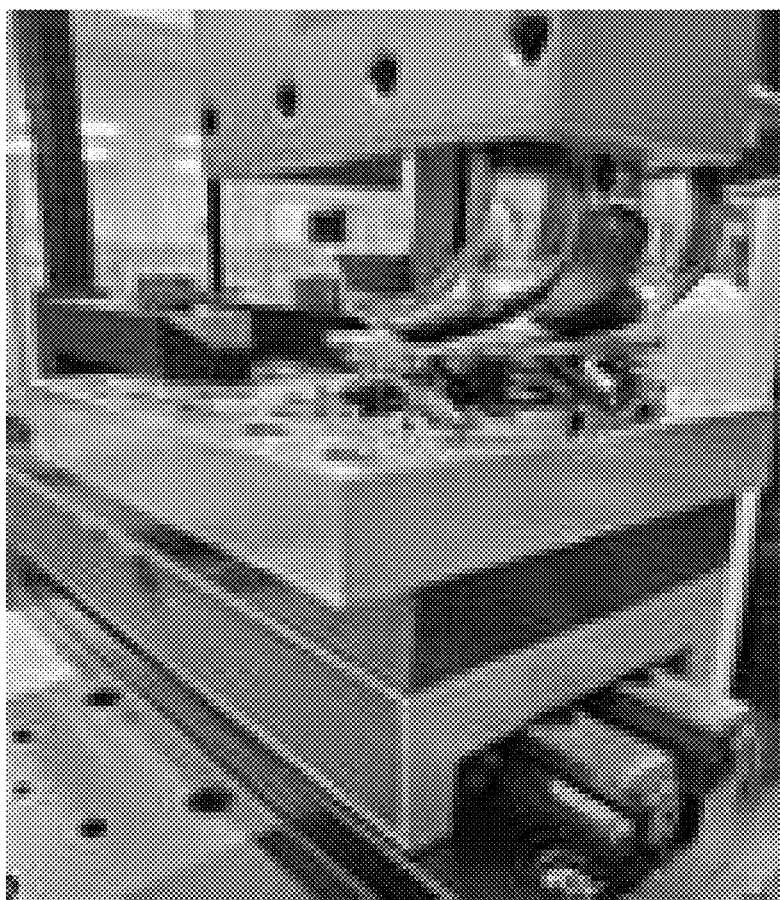
FIG. 19A shows a photograph of a testing arrangement.
Figure 19B:
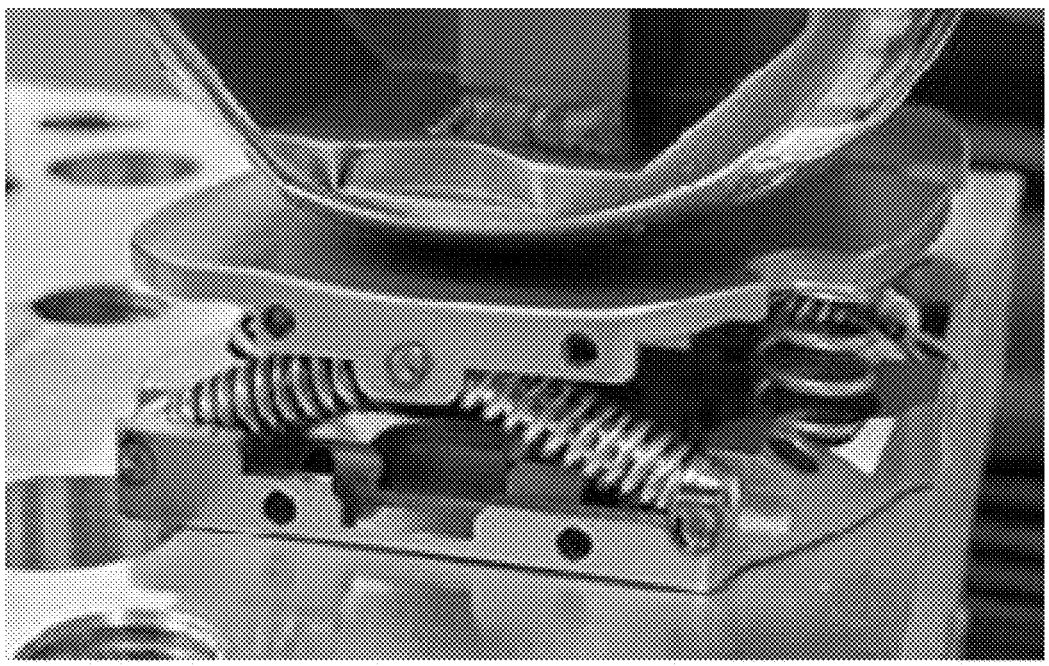
FIG. 19B shows a photograph of a testing arrangement.

In some embodiments, the magnetic field strength of an electromagnet is controlled to alter the interaction between an electromagnet and an opposing electromagnet or permanent magnet attached to the structure, maintaining a constant or quasi-constant force Test Results A ligament balancing device as illustrated in FIGS. 8 and 9A was engineered to deliver a distraction force of 17.5 pounds per compartment (i.e., 35 pounds for both compartments). Five (5) samples of such a device were prepared and tested as described herein. Each test sample was placed into a load frame, in which the distal aspect of the distal plate (e.g., second plate) of the ligament balancing device was placed against a flat steel plate representing a proximal tibial cut; while the proximal aspect of the proximal plate (e.g., first plate) was in contact with a femoral component. Three different sizes of femoral component were tested. During testing, the gap was defined as the distance between the flat plate and the distal aspect of the femoral component, and three values of gap were considered: 9 mm, 12 mm, and 15 mm. The resultant distraction load was measured through the load frame. Measurement was completed three times with each of the five sample ligament balancers, each of which was tested against three sizes of femoral components at three different gaps. FIGS. 19A and 19B show photographs of the test setup used to test the sample ligament balancing devices. FIG. 19C shows a table of the force measurements recorded during the testing described above, showing significant conformity with the intended distraction force (i.e., 34 pounds) and proper repeatability. More particularly, the data shown in the table of FIG. 19C reflects a minimum recorded force (i.e., across all five samples, all three femur sizes, all three gap distances, and all three test runs) of 32.1 pounds and a maximum recorded force (i.e., across all five samples, all three femur sizes, all three gap distances, and all three test runs) of 38.6 pounds. Thus, it may be seen that all recorded force values (i.e., across all five samples, all three femur sizes, all three gap distances, and all three test runs) were within plus or minus 10.3% of the nominal engineered force.

While a number of embodiments of the present invention have been described, it is understood that these embodiments are illustrative only, and not restrictive, and that many modifications may become apparent to those of ordinary skill in the art. For example, all dimensions discussed herein are provided as examples only, and are intended to be illustrative and not restrictive.

What is claimed is:

1. A device, comprising:
   a first plate configured to interface with a first bone structure of a joint;
   a second plate configured to interface with a second bone structure of the joint opposite the first bone structure; and
   at least one mechanical actuation mechanism disposed between the first plate and the second plate and configured to apply a distraction force along an axis between the first plate and the second plate so as to urge the first plate and the second plate away from one another, wherein the at least one mechanical actuation mechanism comprises:
      a first actuation sub-mechanism, and
      a second actuation sub-mechanism,
      wherein the first actuation sub-mechanism is configured to provide a first actuation sub-mechanism distraction force, and wherein the second actuation sub-mechanism is configured to provide a second actuation sub-mechanism distraction force that is antagonist to the first actuation sub-mechanism distraction force;
   wherein the device is configured so as to have a range of expansion ranging from a minimum distance between the first plate and the second plate to a maximum distance between the first plate and the second plate,
   wherein the first actuation sub-mechanism distraction force varies as the device moves through the range of expansion from the maximum distance to the minimum distance,
   wherein the second actuation sub-mechanism distraction force varies as the device moves through the range of expansion from the maximum distance to the minimum distance, and
   wherein the varying first actuation sub-mechanism distraction force and the varying second actuation sub-mechanism distraction force combine to provide the distraction force that is a substantially constant distraction force across the range of expansion.

2. The device of claim 1, wherein the substantially constant distraction force is a distraction force that is within plus or minus fifteen percent of a nominal distraction force across the range of expansion.

3. The device of claim 2, wherein the substantially constant distraction force is a distraction force that is within plus or minus ten percent of a nominal distraction force across the range of expansion.

4. The device of claim 1, wherein the device is a monoblock device.

5. The device of claim 1, wherein the device is a modular device configured for at least one of the first plate or the second plate to be removable from the at least one mechanical actuation mechanism.

6. The device of claim 1, wherein the device is configured to be used in a total knee arthroplasty, a unicompartmental knee arthroplasty, an anatomic total shoulder arthroplasty, a reverse total shoulder arthroplasty, a hip arthroplasty, or an ankle arthroplasty.

7. The device of claim 1,
   wherein the first actuation sub-mechanism comprises at least one axial compression spring oriented along the axis, and
   wherein the second actuation sub-mechanism comprises at least one diagonal compression spring oriented diagonally with respect to the axis.

8. The device of claim 7, wherein the at least one diagonal compression spring is pivotably coupled to the first plate and to the second plate.

9. The device of claim 7, wherein the at least one axial compression spring is a peripheral spring positioned around a perimeter of the second plate.

10. The device of claim 1, further comprising a stability mechanism configured to maintain the first plate and the second plate substantially parallel with respect to one another.

11. The device of claim 1,
    wherein the joint is a bicondylar joint, and
    wherein the first plate is configured to interface only with a first condyle of the first bone structure of the joint.

12. The device of claim 1, further comprising:
    a second one of the first plate configured to interface with the first bone structure of the joint, and
    a second one of the mechanical actuation mechanism disposed between the second one of the first plate and the second plate and configured to apply a second distraction force along an axis between the second one of the first plate and the second plate so as to urge the second one of the first plate and the second plate away from one another,
    wherein the device is configured so as to have a second range of expansion ranging from a minimum distance between the second one of the first plate and the second plate to a maximum distance between the second one of the first plate and the second plate, and wherein the second one of the mechanical actuation mechanism is configured such that the second distraction force is a substantially constant distraction force across the second range of expansion.

13. The device of claim 12, wherein the second distraction force is different from the distraction force.

14. The device of claim 1, wherein the mechanical actuation mechanism is at least partially embedded within one of the first plate or the second plate.

15. The device of claim 1, wherein the device is sized to be positioned intra-articularly within the joint.

16. The device of claim 1, wherein the mechanical actuation mechanism is positioned within a perimeter of the first plate and within a perimeter of the second plate.

17. A kit comprising a first one of the device of claim 1 and a second one of the device of claim 1.

18. The kit of claim 17, wherein the substantially constant distraction force of the first one of the device of claim 1 is greater than the substantially constant distraction force of the second one of the device of claim 1.

19. The kit of claim 17, wherein the first one of the device of claim 1 and the second one of the device of claim 1 are configured to be joined to one another at the respective second plates thereof such that the axis of the distraction force of the first one of the device of claim 1 and the axis of the distraction force of the second one of the device of claim 1 are parallel to one another.

20. The device of claim 1,
wherein the first actuation sub-mechanism distraction force increases as the device moves through the range of expansion from the maximum distance to the minimum distance, and
wherein the second actuation sub-mechanism distraction force decreases as the device moves through the range of expansion from the maximum distance to the minimum distance.

21. A method, comprising:
providing a device including:
   a first plate configured to interface with a first bone structure of a joint of a patient;
   a second plate configured to interface with a second bone structure of the joint opposite the first bone structure; and
   at least one mechanical actuation mechanism disposed between the first plate and the second plate and configured to apply a distraction force along an axis between the first plate and the second plate so as to urge the first plate and the second plate away from one another, wherein the at least one mechanical actuation mechanism comprises:
      a first actuation sub-mechanism, and
      a second actuation sub-mechanism,
      wherein the first actuation sub-mechanism is configured to provide a first actuation sub-mechanism distraction force, and wherein the second actuation sub-mechanism is configured to provide a second actuation sub-mechanism distraction force that is antagonist to the first actuation sub-mechanism distraction force;
   wherein the device is configured so as to have a range of expansion ranging from a minimum distance between the first plate and the second plate to a maximum distance between the first plate and the second plate,
   wherein the first actuation sub-mechanism distraction force varies as the device moves through the range of expansion from the maximum distance to the minimum distance,
   wherein the second actuation sub-mechanism distraction force varies as the device moves through the range of expansion from the maximum distance to the minimum distance, and
   wherein the varying first actuation sub-mechanism distraction force and the varying second actuation sub-mechanism distraction force combine to provide the distraction force that is a substantially constant distraction force across the range of expansion;
performing a cut to the second bone structure of the joint so as to produce a cut surface of the second bone structure;
positioning the device within the joint of the patient such that the second plate abuts the cut surface; and
characterizing laxity of ligaments of the joint of the patient while the device is positioned within the joint.

22. The method of claim 21,
wherein the first actuation sub-mechanism distraction force increases as the device moves through the range of expansion from the maximum distance to the minimum distance, and
wherein the second actuation sub-mechanism distraction force decreases as the device moves through the range of expansion from the maximum distance to the minimum distance.

* * * * *